US006147192A

United States Patent [19]
Gimeno et al.

[11] Patent Number: 6,147,192
[45] Date of Patent: Nov. 14, 2000

[54] TUB INTERACTOR (TI) POLYPEPTIDES AND USES THEREFOR

[75] Inventors: Carlos J. Gimeno, Wellesley; Patrick R. Errada, Cambridge, both of Mass.

[73] Assignee: Millennium Pharmaceuticals, Inc., Cambridge, Mass.

[21] Appl. No.: 09/252,329

[22] Filed: Feb. 18, 1999

Related U.S. Application Data

[60] Division of application No. 08/897,340, Jul. 21, 1997, Pat. No. 5,955,306, which is a continuation-in-part of application No. 08/715,032, Sep. 17, 1996, abandoned.

[51] Int. Cl.⁷ .................................................. C07K 14/00
[52] U.S. Cl. ............................................................ 530/350
[58] Field of Search .......................................... 530/350

[56] References Cited

U.S. PATENT DOCUMENTS 4,886,753  12/1989  Marcker et al. ........................ 800/287

FOREIGN PATENT DOCUMENTS

| 297913 | 1/1989 | European Pat. Off. . |
|---|---|---|
| WO 89/00192 | 1/1989 | WIPO . |
| WO 92/01794 | 2/1992 | WIPO . |

OTHER PUBLICATIONS

Andersson, B. et al., "A "Double Adaptor" Method for Improved Shotgun Library Construction," *Analytical Biochemistry*, vol. 236, 107–113 (1996).
Aplan, P. et al., "Disruption of the SCL Gene by a t(1;3) Translocation in a Patient with T Cell Acute Lymphoblastic Leukemia," *The Journal of Experimental Medicine*, vol. 176, 1303–1310 (Nov. 1992).
Arai, Y. et al., "A Negative Regulatory Region of the Murine Hox11 Gene," *Gene*, vol. 193, 73–79 (1997).
Bludau, H. and Freese, U.K., "Analysis of the HSV–1 Strain 17 DNA Polymerase Gene Reveals the Expression of Four Different Classes of pol Transcripts," *Virology*, vol. 183, 505–518 (1991).
de Kleijn, D.P. et al., "Cloning and Expression of mRNA Encoding Prepro–gonad–inhibiting Hormone(GIH) in the Lobster Homarus Americanus," *FEBS Lett*. vol. 353, No. 3, 255–258 (1994).
del Senno, L. et al., "Dinucleotide Repeat Polymorphism in the Human Estrogen Receptor (ESR) Gene," *Human Molecular Genetics*, vol. 1, No. 5, 354 (1992).
Englestein, M. et al., "A PCR–Based Linkage Map of Human Chromosome 1," *Genomics*, vol. 15, 251–258 (1993).
Fliegel, L. et al., "Molecular Cloning of the High Affinity Calcium–binding Protein (Calreticulin) of Skeletal Muscle Sarcoplasmic Reticulum," *The Journal of Biological Chemistry*, vol. 264, No. 36, 21522–21528 (Dec. 25, 1989).
Geisen, C. et al., "A Transcribed Human Sequence Related to the Mouse HC1 and the Human Papillomavirus type 18 E5 Genes is Located at Chromosome 7p13–14," *Human Molecular Genetics*, vol. 4, No. 8, 1337–1345 (1995).
Grandien, K.F.H. et al., "Localization of DNase I Hypersensitive Sites in the Human Oestrogen Receptor Gene Correlates with the Transcriptional Activity of Two Differentially Used Promoters," *Journal of Molecular Endocrinology*, vol. 10, 269–277 (1993).
Groigno, L. et al., "Insulin–Like Growth Factor I Receptor Messenger Expression During Oogenesis in Xenopus laevis," *Endocrinology*, vol. 137, No. 9, 3856–3863 (1996).
Haug, T. et al., "Human Uracil–DNA Glycosylase Gene: Sequence Organization, Methylation Pattern, and Mapping to Chromosome 12q23–q24.1," *Genomics*, vol. 36, 408–416 (1996).
Haug,, T. et al., "Structure of the Gene for Human Uracil–DNA Glycosylase and Analysis of the Promoter Function," *FEBS Letters*, vol. 353, 180–184 (1994).
Hirano, T. et al., "Essential Roles of the RNA Polymerase I Largest Subunit and DNA Topoisomerases in the Formation of Fission Yeast Nucleolus," *The Journal of Cell Biology*, vol. 108, 243–253 (Feb. 1989).
Hyldig–Nielsen, J. et al., "The Primary Structures of Two Leghemoglobin Genes from Soybean," *Nucleic Acids Research*, vol. 10, No. 2, 689–701 (1982).
Knapp, B. et al., "A New Blood Stage Antigen of Plasmodium falciparum Highly Homologous to the Serine–stretch Protein SERP," *Molecular and Biochemical Parasitology*, vol. 44 1–14 (1991).
Knapp, B. et al., "Molecular Cloning, Genomic Structure and Localization in a Blood Stage Antigen of Plasmodium Falciparum Characterized by a Serine Stretch," *Molecular and Biochemical Parasitology*, vol. 32, 73–84 (1989).
Nilsen, H. et al., "Nuclear and Mitochondrial Uracil–DNA Glycosylases are Generated by Alternative Splicing and Transcription from Different Positions in the UNG Gene," *Nucleic Acids Research*, vol. 25, No. 4, 750–755 (1997).
Pausova, Z. et al., "Evolution of a Repeat Sequence in the Parathyroid Hormone–related Peptide Gene in Primates," *Mammalian Genome*, vol. 6, 408–414 (1995).
Pëléraux, A. et al., "Genomic Organization of a Mouse MHC Class II Region Including the H2–M and Lmp2 Loci," *Immunogenetics*, vol. 43, 204–214 (1996).
Piva, R. et al., "Analysis of Upstream Sequences of the Human Estrogen Receptor Gene," *Biochemical and Biophysical Research Communications*, vol. 183, No. 3, 996–1002 (Mar. 31, 1992).
Piva, R. et al., "Sequencing of an RNA Transcript of the Human Estrogen Receptor Gene: Evidence for a New Transcriptional Event," *J. Steroid Biochem. Molec. Biol.*, vol. 46, No. 5, 531–538 (1993).
Schoots, O. et al., "Cloning of a G Protein–Activated Inwardly Rectifying Potassium Channel from Human Cerebellum," *Molecular Brain Research*, vol. 39, 23–30 (1996).

(List continued on next page.)

*Primary Examiner*—Remy Yucel
*Attorney, Agent, or Firm*—Lahive & Cockfield, LLP; Amy E. Mandagouras, Esq.

[57] ABSTRACT

The present invention provides a novel tub interactor (TI) polypeptides, as well as TI fusion polypeptides, and antigenic peptides.

41 Claims, 15 Drawing Sheets

OTHER PUBLICATIONS

Semenza, G. et al., "Detection of a Novel DNA Polymorphism in the β–Globin Gene Cluster," *The Journal of Biological Chemistry*, vol. 259, No. 10, 6045–6048 (1984).

Shirakawa, H. and Yoshida, M., "Structure of a Gene Coding for Human HMG2 Protein," *The Journal of Biological Chemistry*, vol. 267, No. 10, 6641–6645 (Apr. 5, 1992).

Yamagishi, M. and Nomura, M., "Cloning and Sequence Determination of the Gene Encoding the Largest Subunit of the Fission Yeast Schizosaccharomyces pombe RNA Polymerase I," *Gene*, vol. 74, 503–515 (1988).

Yamashita, I. et al., "Gene Fusion is a Possible Mechanism Underlying the Evolution of STA1," *J. Bacteriol.*, vol. 169, No. 5, 2142–2149 (May 1987).

Genbank™ Accession No. M99146 for Human Polymorphic Microsatellite DNA.

Genbank™ Accession No. X13857 for Yeast STA2 Gene for Extracellular Glucoamylase (Glucan 1.4–alpha–glucosidase) 5'–flank (EC 3.2.1.3).

Genbank™ Accession No. X58283 for M. Musculus B2 Repeat DNA.

Genbank™ Accession No. X99121 for R. Norvegicus RT6 Gene, Exon 2, Testis.

Genbank™ Accession No. Z11832 for P. Falciparum 3.8 Gene for Putative Serine Kinase (partial) and GBP130 Gene for Glycophorin Binding Protein (partial).

Genbank™ Accession No. Z46378 for H. Sapiens DNA for HK2 Pseudogene Locus.

Genbank™ Accession No. Z46728 for S. Cerevisiae Chromosome IX Cosmid 9910.

Genbank™ Accession No. Z68273 for Human DNA Sequence from Cosmid L165D7, Huntington's Disease Region, Chromosome 4p16.3 Contains Human G Protein Coupled Receptor Kinase–like.

Genbank™ Accession No. Z70041 for Human DNA Sequence from Cosmid U39H5, between Markers DXS6791 and DXS8038 on Chromosome X.

Genbank™ Accession No. Z72519 for Human DNA Sequence from Cosmid J138017, Between Markers DXS6791 and DXS8038 on Chromosome X Contains EST CA Repeat and an Endogenous Retroviral Like Element.

Genbank™ Accession No. Z75741 for Human DNA Sequence from PAC 107N3, Between Markers DXS6791 and DXS8038 on Chromosome X.

Genbank™ Accession No. Z82211 for Human DNA Sequence from PAC 447N6 on Chromosome X Contains ESTs and STS.

Genbank™ Accession No. Z82248 for Human DNA Sequence from Cosmid N44A4 on Chromosome 22q12–qter Contains 14–3–3 Protein, ESTs and CpG Island.

Genbank™ Accession No. Z83313 for Human DNA Sequence from PAC 106C24, Between Markers DXS294 and DXS730 on Chromosome X.

Genbank™ Accession No. Z83818 for Human DNA Sequence from PAC 138A5 on Chromosome X Contains ESTs.

Genbank™ Accession No. Z83820 for Human DNA Sequence from PAC 215K18 on Chromosome X Contains ESTs, and STS.

Genbank™ Accession No. Z83841 for Human DNA Sequence from PAC 323B6 on Chromosome X Contains ESTs CpG Island.

Genbank™ Accession No. AC000038 for p101h3, Complete Sequence.

Genbank™ Accession No. AC000111 for Human BAC Clone 068P20 from 7q31–q32, Complete Sequence.

Genbank™ Accession No. AC001597 for Homo Sapiens (subclone 3_e12 from PAC H91) DNA Sequence, Complete Sequence.

Genbank™ Accession No. AC002113 for Human Cosmid g1862x083 from 7q31.3, Complete Sequence.

Copy of Gen Bank™ search using mTI–3 (gene).

Atencio, D. and Yaffe, M., "MAS5, a Yeast Homolog of DnaJ Involved in Mitochondrial Protein Import," *Molecular and Cellular Biology*, vol. 12, No. 1, 283–291 (Jan. 1992).

Bergez, P. et al., "The Sequence of a 44 420 bp Fragment Located on the Left Arm of Chromosome XIV from Saccharomyces cerevisiae," *Yeast*, vol. 11, 967–974 (1995).

Braun, J.E.A. and Scheller, R.H., "Cysteine String Protein, a DnaJ Family Member, is Present on Diverse Secretory Vesicles," *Neuropharmacology*, vol. 34, No. 11, 1361–1369 (1995).

Bucca, G. et al., "Cloning and Sequencing of the dnaK Region of Streptomyces coelicolor A3(2)," *Gene*, vol. 130, 141–144 (1993).

Bucca G. et al., "The dnaK Operon of Streptomyces coelicolor Encodes a Novel Heat–shock Protein Which Binds to the Promoter Region of the Operon," *Molecular Microbiology*, vol. 17, No. 4, 663–674 (1995).

Caplan, A. and Douglas, M., "Characterization of YDJ1: A Yeast Homologue of the Bacterial dnaJ Protein," *The Journal of Cell Biology*, vol. 114, No. 4, 609–621 (Aug. 1991).

Chan, M. et al., "Structure of a Hyperthermophilic Tungstopterin Enzyme, Aldehyde Ferredoxin Oxidoreductase," *Science*, vol. 267, 1463–1469 (Mar. 10, 1995).

Cross, S.H. et al., "Purification of CpG Islands Using a Methylated DNA Binding Column," *Nature Genet.*, vol. 6, No. 3, 236–244 (Mar. 1994).

Evans, G. and Wahl, G., "Cosmid Vectors for Genomic Walking and Rapid Restriction Mapping," *Methods in Enzymology*, vol. 152, 604–610 (1987).

Liu, N. et al., "Comparison of cDNAs from Bovine Brain Coding for Two Isoforms of Calreticulin," *Biochimica et Biophysica Acta*, vol. 1202, 70–76 (1993).

Mastrogiacomo, A. and Gundersen, C., "The Nucleotide and Deduced Amino Acid Sequence of a Rat Cysteine String Protein," *Molecular Brain Research*, vol. 28, 12–18 (1995).

Wilson, R. et al., "2.2 Mb of Contiguous Nucleotide Sequence from Chromosome III of C. elegans," *Nature*, vol. 368, 32–38 (Mar. 3, 1994).

Genbank™ Accession No. D87073 for Human mRNA for KIAA0236 Gene, Complete cds.

Genbank™ Accession No. G05830 for Human STS WI–7256.

Genbank™ Accession No. L36113 for *Arabidopsis Thaliana* Chaperone Protein (atj) mRNA, Complete cds.

Genbank™ Accession No. U22340 for *Arabidopsis Thaliana* DnaJ Homolog (atj) MRNA, Complete cds.

Genbank™ Accession No. U57637 for Rhodobacter Capsulatus Heat Shock Proteins (dnaK and dnaJ) Genes, complete cds.

Genbank™ Accession No. X94301 for *S. tuberosum* mRNA for DnaJ Protein.

Genbank™ Accession No. X95245 for *D. melanogaster* 1(2): rot Gene (strain apxo).

Genbank™ Accession No. Y10074 for *D. Melanogaster* 1(2)tid, 1(2) not & 1(2) rot Genes (Strain opxo).

Genbank™ Accession No. Z71340 for *S. Cerevisiae* Chromosome XIV Reading Frame ORF YNL064c.

Genbank™ Accession No. Z71504 for *S. cerevisiae* Chromosome XIV Reading Frame ORF YNL228w.

Genbank™ Accession No. AA390603 for LD09665.5prime LD Drosophila Embryo *Drosophila melanogaster* cDNA Clone LD09665 5".

Genbank™ Accession No. AA538849 for LD18471.5prime LD Drosophila Embryo *Drosophila Melanogaster* dDNA Clone LD18471 5" Similar to M63008: *D. melanogaster* Cysteine–string Protein 29 (csp29) mRNA, 5' end; M63421: *D.melanogaster* Cysteine–string Protein 32 (csp32) mRNA, Complete cds.

Genbank™ Accession No. AA540391 for LD19869.5prime LD Drosophila Embryo *Drosophila Melanogaster* cDNA Clone LD19869 5' Similar to X95246: *D.melanogaster* 1(2) rot Gene (strain blf); X95249: *D.melanogaster* 1(2) tid Gene (strain apxo, 1(2) tid2 mutant).

Copy of GenBank™ search using hTI–1 (gene).

Chen, L. et al., "Evolution of Antifreeze Glycoprotein Gene from a Trypsinogen Gene in Antarctic Notothenioid Fish," *PNAS*, vol. 94, 3811–3816 (Apr. 1997).

Chen, Z. et al., "Expression and Activity–Dependent Changes of a Novel Limbic–Serine Protease Gene in the Hippocampus," *The Journal of Neuroscience*, vol. 15, No. 7, 5088–50897 (Jul. 1995).

Dihanich, M. and Spiess, M., "A Novel Serine Proteinase–like Sequence from Human Brain," *Biochimica et Biophysica Acta*, vol. 1218, 225–228 (1994).

Gauthier, E. et al., "Characterization of Canine Pancreas Kallikrein cDNA," *Biochimica et Biophysica Acta*, vol. 1218, 102–104 (1994).

Genicot, S. et al., "Trypsin and Trypsinogen from an Antarctic Fish: Molecular Basis of Cold Adaptation," *Biochimica et Biophysica Acta*, vol. 1298, 45–57 (1996).

Gudmundsdottir, A. et al., "Isolation and Characterization of cDNAs from Atlantic Cod Encoding Two Different Forms of Trypsinogen," *Eur. J. Biochem.*, vol. 217, No. 3, 1091–1097 (1993).

Hahn, B. et al., "Purification and Molecular Cloning of Calobin, a Thrombin–like Enzyme from *Agkistrodon caliginosus* (Korean Viper)," *J. Biochem.*, vol. 119, 835–843 (1996).

Howles, P. et al., "Use of a cDNA Recombinant for the γ–subunit of Mouse Nerve Growth Factor to Localize Members of this Multigene Family Near the TAM–1 Locus on Chromosome 7," *Nucleic Acids Research*, vol. 12, No. 6, 2791–2805 (1984).

Hung, C. et al., "Characterization of One Novel Venom Protease with β–Fibrinogenase Activity from the Taiwan Habu (Trimeresurus Mucrosquamatus): Purification and cDNA Sequence Analysis," *Biochemical And Biophysical Research Communications*, vol. 205, No. 3, 1707–1715 (Dec. 30, 1994).

Itoh, N. et al., "Molecular Cloning and Sequence Analysis of cDNA for Batroxobin, a Thrombin–like Snake Venom Enzyme," *The Journal of Biological Chemistry*, vol. 262, No. 7, 3132–3135 (Mar. 5, 1987).

Ma, J. et al., "Molecular Cloning and Characterization of rKlk10, a cDNA Encoding T–Kininogenase from Rat Submandibular Gland and Kidney," *Biochemistry*, vol. 31, No. 44, 10922–10928 (1992).

Mason, A. et al., "Structure of Mouse Kallikrein Gene Family Suggests a Role in Specific Processing of Biologically Active Peptides," *Nature*, vol. 303, 300–307 (May 26, 1983).

Pinsky, S. et al., "Differential Regulation of Trypsinogen mRNA Translation: Full–Length mRNA Sequences Encoding Two Oppositely Charged Trypsinogen Isoenzymes in the Dog Pancreas," *Molecular and Cellular Biology*, vol. 5, No. 10, 2669–2676 (Oct. 1985).

Ullrich, A. et al., "Isolation of a cDNA Clone Coding for the γ–Subunit of Mouse Nerve Growth Factor Using a High–Stringency Selection Procedure," *DNA*, vol. 3, No. 5, 387–392 (1984).

Zhang, Y. et al., "A Novel Plasminogen Activator from Snake Venom," *The Journal of Biological Chemistry*, vol. 270, No. 17, 10246–10255 (Apr. 28, 1995).

Genbank™ Accession No. D38507 for Cattle mRNA for Pancreas Cationic Pretrypsinogen, Partial cds.

Genbank™ Accession No. G13528 for Human STS SHGC–11067.

Genbank™ Accession No. U25747 for Takifugu Rubripes Trypsinogen mRNA, partial cds.

Genbank™ Accession No. U31417 for Trimeresurus Mucrosquamatus Preprotrimubin mRNA, complete cds.

Genbank™ Accession No. U47819 for Gadus Morhua Trypsinogen I mRNA, partial cds.

Genbank™ Accession No. X56744 for P.platessa mRNA for Trypsinogen.

Genbank™ Accession No. X58702 for T.repens DNA for Tandem Repeat Region, Clone pTrR350.2.

Genbank™ Accession No. X83222 for T.mucrosquamatus mRNA for Mucrofibrase–2.

Genbank™ Accession No. X83224 for T.mucrosquamatus mRNA for Mucrofibrase–4.

Genbank™ Accession No. X83225 for T.mucrosquamatus mRNA for Mucrofibrase–5.

Genbank™ Accession No. AA095255 for 11969.seq.F Fetal Heart, Lambda ZAP Express Homo sapiens cDNA 5'.

Genbank™ Accession No. AA487430 for ab20a12.s1 Stratagene Lung (#937210) Homo Sapiens cDNA Clone 841342 3' Similar to gb:M30038 Alpha–Tryptase Precursor (Human).

Copy of GenBank™ search using hTI–2 (gene).

Klotz, M. and Anderson, A., "Sequence of a Gene Encoding Periplasmic *Pseudomonas syringae* Ankyrin," *Gene*, vol. 164, 187–188 (1995).

Klotz, M.G. et al., "Cloning, Characterization and Phenotypic Expression in *Escherichia coli* of catF, which Encodes the Catalytic Subunit of Catalase Isozyme CatF of *Pseudomonas syringae*," *Appl Microbiol Biotechnol*, vol. 43, 656–666 (1995).

Genbank™ Accession No. U88624 for Mus Musculus 85 kDa Calcium–independent Phospholipase A2 mRNA, complete cds.

Genbank™ Accession No. U91319 for Human Chromosome 16p13.11 BAC Clone CIT987SK–98H8 complete sequence.

Genbank™ Accession No. Z77249 for Human DNA Sequence from PAC 358H7 on Chromosome X.

Copy of GenBank™ search using hTI–1 (protein).

Chen, E. and Seeburg, P., "Supercoil Sequencing: A Fast and Simple Method for Sequencing Plasmid DNA," *DNA*, vol. 4, No. 2, 165–170; (Nov. 2, 1985).

Mortari, F. et al., "Human Cord Blood Antibody Repertoire," *The Journal of Immunology*, vol. 150, No. 4, 1348–1357 (Feb. 15, 1993).

Genbank™ Accession No. L33839 for Rattus Norvegicus (clone K–32) Kallikrein mRNA, 3' end.

Genbank™ Accession No. L43121 for Papio Hamadryas Tissue Kallikrein (KLK1) mRNA, complete cds.

Genbank™ Accession No. U72330 for *Xenopus Laevis* Trypsinogen mRNA, complete cds.

Genbank™ Accession No. W11768 for mb22f03.r1 Soares Mouse p3NMF19.5 Mus Musculus cDNA Clone 330173 5' Similar to SW:KLK1_Human P06870 Glandular Kallikrein 1 Precursor.

Genbank™ Accession No. W60374 for zd29b01.r1 Soares Fetal Heart NbHH19W Homo Sapiens cDNA Clone 342025 5' Similar to PIR:S55066 S55066 Trypsinogen Precursor.

Genbank™ Accession No. AA071438 for zm73a01.s1 Stratagene Neuroepithelium (#937231) Homo Sapiens cDNA Clone 531240 3' Similar to gb:X13561 Glandular Kallikrein 1 Precursor (Human).

Genbank™ Accession No. AA390094 for vb28b08.r1 Soares Mouse Lymph Node NbMLN Mus Musculus cDNA Clone 750231 5' Similar to SW:TRY3_RAT P08426 Trypsinogen III, Cationic Precursor.

Genbank™ Accession No. AA467748 for nc74f11.s1 NCI_CGAP_Pr2 Homo Sapiens cDNA Clone Image:783117 Similar to SW:PROS_Human P07288 Prostate Specific Antigen Precursor.

Copy of GenBank™ search using hTI-3 (gene).

Triglia, T. et al., "Structure of a Plasmodium falciparum Gene that Encodes a Glutamic Acid–rich Protein (GARP)," *Molecular and Biochemical Parasitology*, vol. 31, 199–202 (1988).

Copy of GenBank™ search using mTI-4 (protein).

Copy of GenBank™ search using mTI-3 (protein).

Peterson, S. et al., "A Survey of the Mycoplasma genitalium Genome by Using Random Sequencing," *Journal of Bacteriology*, vol. 175, No. 24, 7918–7930 (Dec. 1993).

Tilly, K. et al., "Isolation of dnaJ, dnaK, and grpE Homologues from Borrelia burgdorferi and Complementation of *Escherichia coli* Mutants," *Mol. Microbiol.*, vol. 7, 359–369 (1993).

Genbank™ Accession No. H83919 for yv84h07.s1 Homo Sapiens cDNA Clone 249469 3' Similar to SP:S41948 S41948 DNAJ Protein—Streptomyces.

Genbank™ Accession No. U40992 for Human Heat Shock Protein hsp40 Homolog mRNA, complete cds.

Genbank™ Accession No. AA033375 for mi42b01.r1 Soares Mouse Embryo NbME13.5 14.5 Mus Musculus cDNA Clone 466153 5' Similar to SW:DNAJ_CLOAB P30725 DNAJ Protein.

Genbank™ Accession No. AD000092 for Homo Sapiens DNA from Chromosome 19p13.2 Cosmids R31240, R30272 and R28549 Containing the EKLF, GCDH, CRTC, and RAD23A Genes, Genomic Sequence.

Copy of GenBank™ search using mTI-4 (gene).

Copy of GenBank™ search using hTI-4 (gene).

Copy of GenBank™ search using hTI-2 (protein).

Copy of GenBank™ search using hTI-3 (protein).

Copy of GenBank™ search using hTI-4 (protein).

Kleyn, Patrick et al., "Identification and Characterization of the Mouse Obesity Gene tubby: A Member of a Novel Gene Family" *Cell*, vol. 85, 281–290 (1996).

Noben–Trauth, Konrad et al., "A Candidate Gene for the Mouse Mutation tubby" *Nature*, vol. 380, 534–538 (1996).

Murthy et al., DNA and Cell Biology 15(9):727–735 (1996).

FIG. 1A

```
        N   S   A   R   A   H   S   Q   P   W   Q   A   A   L   V   M   E   N   E     19
       GG  AAT TCG GCA CGA GCG CAC TCG CAG GCC CTG CAG GCG GCA CTG GTC ATG GAA AAC GAA   59

L    F   C   S   G   V   L   V   H   P   Q   W   V   L   S   A   A   H   C   F     39
  TTG  TTC TGC TCG GGC GTC CTG GTG CAT CCG CAG TGG GTG CTG TCA GCC GCA CAC TGT TTC    119

Q    K   *   V   Q   S   S   Y   T   I   G   L   L   H   S   L   E   A   D         59
  CAG  AAG TGA GTG CAG AGC TCC TAC ACC ATC GGG CTG CTG CAC AGT CTT GAG GCC GAC        179

Q    E   P   G   S   Q   M   V   E   A   S   L   S   V   R   H   P   E   Y   N     79
  CAA  GAG CCA GGA AGC CAG ATG GTG GAG GCC AGC CTC TCC GTA CGG CAC CCA GAG TAC AAC    239

R    P   L   L   A   N   D   L   M   L   I   K   L   D   E   S   V   S   E   S     99
  AGA  CCC TTG CTC GCT AAC GAC CTC ATG CTC ATC AAG TTG GAC GAA TCC GTG TCC GAG TCT    299

D    T   I   R   S   I   S   I   A   S   Q   C   P   T   A   G   N   S   C   L    119
  GAC  ACC ATC CGG AGC ATC AGC ATT GCT TCG CAG TGC CCT ACC GCG GGG AAC TCT TGC CTC    359

V    S   G   W   G   L   L   A   N   G   R   M   P   T   V   L   Q   C   V   N    139
  GTT  TCT GGC TGG GGT CTG CTG GCG AAC GGC AGA ATG CCT ACC GTG CTG CAG TGC GTG AAC    419

V    S   V   V   S   E   E   V   C   S   K   L   Y   D   P   L   Y   H   P   S    159
  GTG  TCG GTG GTG TCT GAG GAG GTC TGC AGT AAG CTC TAT GAC CCG CTG TAC CAC CCC AGC    479

M    F   C   A   G   G   G   Q   D   Q   K   D   S   C   N   G   D   S   G   G    179
  ATG  TTC TGC GCC GGA GGG CAA CAG GAC CAG AAG GAC TCC TGC AAC GGT GAC TCT GGG GGG    539

P    L   I   C   N   G   Y   L   Q   G   L   V   S   F   G   K   A   P   C   G    199
  CCC  CTG ATC TGC AAC GGG TAC TTG CAG GGC CTT GTG TCT TTC GGA AAA GCC CCG TGT GGC    599
```

FIG. 1B

```
 Q   V   G   V   P   G   V   Y   T   N   L   C   K   F   T   E   W   I   E   K     219
CAA GTT GGC GTG CCA GGT GTC TAC ACC AAC CTC TGC AAA TTC ACT GAG TGG ATA GAG AAA     659

T   V   P   G   Q   L   T   L   G   T   G   N   P   *                              233
ACC GTA CCA GGC CAG TTA ACT CTG GGG ACT GGG AAC CCA TGA                             701

AATTGACCCCCAAATACATCTGCGAAGGAATTCAGGAATATCTGTTCCCAGCCCCTCCCTCAGCCYCAGGAGTC          780

CAGGCCCCCAGCCCCTCTCCCTCAAACCAAGGGTACAGATCCCTCCCTCAGACCCCAGGAGTCCAGACC               859

CCCCAGCCCCTCTCCCTCAGACCCCAGGAGTCCAGCCTCTCCCTCAGACCCCAGGAGTCCAGACCCCCCAGCCCCTC       938

CTCCCTCAGACCCCAGGGGTCCAGCCCCTCCCTCAGACCCCAGGAGTCCAGATCCCCCAGCCCCTCCCTCAGACC         1017

CAGGAGTCCAGCCCCTCCCTCAGACTCAGAGGTCCAAGCCCCCAACCCCTCCCTCCCAGACCCCAGGGGTCCAGG         1096

CCCCCAACCCCTCCCTCAGACTCAGAGGTCCAAGCCCCCAACCCCTCCTTCCCAGACCCCAGAGGTCCAGGTACCA        1175

GCCCTCCTCCCTCAGACCCAGCGGTCCAATGCCACCTATACTCTCCCTGTACANATTGCNCCTTGTGGCACGTTGAC       1254

CCAACCTTACCAGTTGGTTTTTCATTTTTTGTCCCTTTCCCCTAGATCCAGAAATAAAGTTTAAGRGRAGSGCCAAAAA     1333

AAAAAAAAAAAAAAAAAAAAAAAAAAAAAAAAAACYCGAGAANT                                        1387
```

FIG. 2A

```
CACACCAGTAGACCCACACAGCACCGGTTGGCCCTGCCCCGCCCAGCTCGCTGACAGCACGACTCAGGGCGAGG      79

M   A   A      3
GAAGTAGGTCCGTTGGTCGTCGGGAACGAGGCTCAGGCGCCAGGCCCGCCGCGGGAGCCCGTTGCC ATG GCA GCC  153

A   A   G   D   A   D   D   A   E   P   R   S   G   H   S   S   E   G   E   C   23
GCC GCC GGG GAC GCG GAC GAC GCG GAG CCG CGC TCA GGC CAC TCG AGC TCG GAG GGC TGC  213

A   V   A   P   E   P   L   T   D   A   L   F   S   F   A   D   F   G           43
GCG GTG GCG CCC GAG CCG CTG ACT GAC GCT CTC TTC TCC TTC GCT GAC TTC GGG          273

S   A   L   G   G   A   G   L   S   G   R   A   S   G   A   Q   S              63
TCT GCG CTG GGC GGC GCG GGC CTC TCG GGC CGG GCG TCC GGC GCC CAG TCG              333

P   L   R   Y   L   H   V   Q   D   A   E   P   R   D   E   L   R              83
CCG CTG CGC TAC TTG CAC GTC CAG CAG GAT GCG GAG CCG CGC GAC GAG CTG CGC          393

C   K   I   P   A   G   R   L   R   R   A   R   P   H   R   L   G   P          103
TGC AAG ATA CCC GCT GGC CGG CGG CTG AGG CGC GCC AGG CCC CAC CGG CTC GGG CCC     453

T   G   K   E   V   H   A   L   R   D   S   A   N   A   N   D   V              123
ACG GGC AAG GAG GTG CAC GCT CTG AGA GAC TCG GCC AAT GCC AAT GAT GTG              513

E   T   V   Q   Q   L   E   D   G   A   D   P   C   A   D   D   K   G          143
GAA ACA GTG CAG CAG CTG GAA GAT GGC GCG GAT CCC TGT GCA GCT GAT GAC AAG GGC     573

R   T   A   L   H   F   A   S   C   N   G   N   D   Q   I   V   Q   L   L      163
CGC ACA GCT CTA CAC TTT GCC TCA TGC AAT GGC AAT GAC CAG ATT GTG CAG CTG CTG     633
```

FIG. 2B

```
  D   H   G   A   D   P   N   Q   R   D   G   L   G   N   T   P   L   H   L   A    183
GAC CAT GGT GCT GAT CCT AAC CAG CGA GAT GGG CTG GGG AAC ACG CCA CTG CAC CTG GCG    693

A   C   T   N   H   V   P   V   I   T   T   L   L   R   G   A   R   V   D        203
GCC TGC ACC AAC CAC GTT CCT GTC ATC ACC ACA CTG CTA CGA GGA GGG GCC CGT GTA GAT    753

A   L   D   R   A   G   R   T   P   L   H   L   A   K   S   K   L   N   I   L    223
GCC CTG GAC CGA GCT GGT CGC ACA CCC CTG CAC CTG GCC AAG TCA AAG CTG AAT ATC CTG    813

Q   E   G   H   A   Q   C   L   E   A   V   R   L   E   V   K   Q   I   I   H    243
CAG GAG GGC CAT GCC CAG TGC CTA GAG GCT GTG CGT CTG GAG GTG AAG CAG ATC ATC CAT    873

M   L   R   E   Y   L   E   R   L   G   Q   H   E   Q   R   E   R   L   D   D    263
ATG CTG AGG GAG TAT CTG GAG CGC CTA GGG CAA CAT GAG CAG CGA GAA CGC CTG GAT GAC    933

L   C   T   R   L   Q   M   T   S   T   K   E   Q   V   D   E   V   T   D   L    283
CTC TGC ACC CGC CTG CAG ATG ACC AGT ACC AAA GAG CAG GTG GAT GAA GTG ACT GAC CTC    993

L   A   S   F   T   S   L   Q   M   Q   S   M   E   K   R   *                    301
CTG GCC AGC TTC ACC TCC CTC AGT CTG CAG AGC ATG GAG AAG AGG TAG                   1047

CAAGAGAGGCTCCCTGCCTTCCTGCCACTGTGTCTCAGTACCAAGAAAAGCCAACATC                        1126

TGGGACTTGGAGCTGCACTTGTGTCTGGTGAGGACTTGCCCCTCACCCGCACATGCCGTGGGGCAGAGATGCTCTCTCTCC  1205

ACGGCCTCAGAGACCACTCCCAGCCACTCTGTGGACAGGGACCACAGCTCCCAGCTTCTTCCAGTTC               1284

TCGCAGCACCAGACCAGCCTCTGCACTTCAGCTGCAGCTGCACTTCAGCTCCGCTATCTCAGCAGACCTCACTTGCCCCA  1363
```

FIG.2C

```
TGGCCCTTCATGGCGCGTCCAGGCCTCCAGACCCTTCTCTGTGTCCGTCCTGGCCATGGGCTTGTTGCAGTCAGCAGGT    1442
GTGGGCTTAGGCGGGCACCCTGTGGCCAGGGGTACTGCGTGAGGCCCTCAGTTGGTCCTCTGCCCTCTGCCTCCACCAGCACTTA    1521
GACAGACACGTCACCAGACTTTCAAGGAGATACTGCAGTGAGTTTCTCTGGTTGGAAGGGGAGGTTGGTGAGTCCCAG    1600
ACCTTAAAAATACAAGGTTAAGAGGGACCCCAAAGCAAAAAATTCCAACCCTTTCCTCCCAGTCATTGAAACACCAAA    1679
ACTATTATACCGGAGGGTGTAATAGTTTTGCTGCCCAGTTGTGGTAGGCCAGTAGTGCCTCCCAAGATGCCCATGTCC    1758
TAATCCCAGGAACCTGTCAAAATTACCTTGTATGGCCAAAGGGGCTTTGCAGATGTAAGTTAAGGATCTTTCGCC    1837
AGGAAGATTATCCCAGCTTGTTCAGAGGGGCTTGATGTCCTCACCCGGGTCTGTATAACAGAAGACAGGTGACGGGAG    1916
AGGAGGTTGGAGGTGTAGCGATGAGCAGGAAACTGGAGTTGAGGAGGGCAGCTCAAGCCACAGAGTCCAGGCCACCTC    1995
AGAGCCAGGAAATGCATCCTCCCACAGAGCCCCTGGAAGGCCCCAGCCCTGCTCCCACCTGACTGGCTCAGTGAGGCTA    2074
ATTTTATAATTCTGGCTGATTTTAGAACTCTAAGGAATAAATTTGTGTTGTTTAAGTCAAAAAAAAAAAAAAAA    2153
ACTCGAG    2160
```

FIG.3A

```
                                                         M   M   L   G   R   F        6
HAATTCGGCACGAGAAAAATGCTAGCTATTATGTGTAATCGAGCAGCCACCTTG ATG ATG CTT GGA AGG TTC       71

R   E   A   L   G   D   A   Q   Q   S   V   R   L   D   D   D   S   F   V   R   G   26
CGG GAA GCT CTT GGA GAT GCA CAA CAG TCA GTG AGG TTG GAT GAC AGT TTT GTC CGG GGA      131

H   L   R   E   G   K   C   H   L   S   L   G   N   A   M   A   A   C   R   S       46
CAT CTA CGA GAG GGC AAG TGC CAC CTC TCT CTG GGG AAT GCC ATG GCA GCA TGT CGC AGC      191

F   Q   R   A   L   E   L   D   H   K   N   A   Q   A   Q   Q   E   F   K   N       66
TTC CAG AGA GCC CTA GAA CTG GAT CAT AAA AAT GCT CAG CAA GCA CAA GAG TTC AAG AAT      251

A   N   A   V   M   E   Y   E   K   I   A   E   T   D   F   E   K   R   D   F       86
GCT AAT GCA GTC ATG GAA TAT GAG AAA ATA GCA GAA ACA GAT TTT GAG AAG CGA GAT TTT      311

R   K   V   V   F   C   M   D   R   A   L   E   F   A   P   A   C   H   R   F      106
CGG AAG GTT GTT TTC TGC ATG GAC CGT GCC CTA GAA TTT GCC CCT GCC TGC CAT CGC TTC      371

K   I   L   K   A   E   C   L   A   M   L   G   R   Y   P   E   A   Q   S   V      126
AAA ATC CTC AAG GCA GAA TGT TTA GCA ATG CTG GGT CGT TAT CCA GAA GCA CAG TCT GTG      431

A   S   D   I   L   R   M   D   S   T   N   A   D   A   L   Y   V   R   G   L      146
GCT AGT GAC ATT CTA CGA ATG GAT TCC ACC AAT GCA GAT GCT CTG TAT GTA CGA GGT CTT      491

C   L   Y   E   D   C   I   E   K   A   V   Q   F   F   V   Q   A   L   R          166
TGC CTT TAT TAC GAA GAT TGT ATT GAG AAG GCA GTT CAG TTT TTC GTA CAG GCT CTC AGG      551
```

FIG.3B

```
  M   A   P   D   H   E   K   A   C   I   A   C   R   N   A   K   A   L   K   A    186
ATG GCT CCT GAC CAC GAG AAG GCC TGC ATT GCC TGC AGA AAT GCC AAA GCA CTC AAA GCA     611

K   K   E   D   G   N   K   A   F   K   E   G   N   Y   K   L   A   Y   E   L    206
AAG AAA GAA GAT GGG AAT AAA GCA TTT AAG GAA GGA AAT TAC AAA CTA GCA TAT GAA CTG     671

Y   T   E   A   L   G   I   D   P   N   N   I   K   T   N   A   K   L   Y   C    226
TAC ACA GAA GCC CTG GGG ATA GAC CCC AAC AAT ATA AAA ACA AAT GCT AAA CTC TAC TGT     731

N   R   G   T   V   N   S   K   L   R   K   L   D   D   A   I   E   D   C   T    246
AAT CGG GGT ACG GTT AAT TCC AAG CTT AGG AAA CTA GAT GAT GCA ATA GAA GAC TGC ACA     791

N   A   V   K   L   D   D   T   Y   I   K   A   Y   L   R   R   A   Q   C   Y    266
AAT GCA GTG AAG CTT GAT GAC ACT TAC ATA AAA GCC TAC TTG AGA AGA GCT CAG TGT TAC     851

M   D   T   E   Q   Q   Y   E   E   A   V   R   D   Y   E   K   V   Q   T   E    286
ATG GAC ACA GAA CAG TAT CAG GAA GAA GCA GTA CGA GAC TAT GAA AAA GTA CAG ACA GAG     911

K   T   K   E   H   K   Q   L   L   K   N   A   Q   L   K   F   R   N   Y   K    306
AAA ACA AAA GAA CAC AAA CAG CTC CTA AAA AAT GCG CAA CTT AAG TTT AGA AAT TAC AAG     971

F   Q   *                                                                         309
TTT CAG TAA                                                                         980

TAGCTGAACCTGTTCAAAATGTTAATAAAGGTTTCGTTGCATGGTAGCATAAAAAAAAAAAAAAAAAA               1049
```

FIG.4A

```
                              M   C   P   N   N   A   S   Y   Y   G   N   R   A   A   T       15
TCGAGATTTACCCATAGAT          ATG TGT CCT AAC AAT GCC AGC TAT TAC GGT AAT CGA GCG GCC ACA       64

L   M   M   L   G   R   F   R   E   A   L   G   D   A   Q   Q   S   V   R   L               35
CTG ATG ATG CTT GGA CGG TTC CGG GAA GCT CTT GGA GAT GCG CAG CAG TCT GTG AGG TTG              124

D   D   S   F   V   R   G   H   L   R   E   G   K   C   L   S   L   G   N                   55
GAT GAC AGT TTT GTC CGG GGA CAC CTC CGA GAA GGC AAG TGC CTC TCA CTT GGG AAT                  184

A   M   A   A   C   R   S   F   Q   A   N   A   L   E   D   H   K   N   A   Q               75
GCA ATG GCG GCA TGT CGT AGT TTC CAA AGA GCC CTA GAA CTG GAT CAT AAA AAT GCC CAG              244

A   Q   Q   E   F   K   N   A   N   V   M   E   Y   E   K   I   A   E   V                   95
GCA CAG CAG GAG TTC AAG AAC GCC AAT GCC GTC ATG GAG TAT GAG AAA ATA GCA GAA GTG              304

D   F   E   K   R   D   F   R   K   V   V   F   C   M   D   R   A   L   E   F              115
GAT TTT GAA AAG CGA GAT TTC CGG AAG GTT GTT TTC TGC ATG GAC CGT GCC CTA GAA TTT              364

A   P   A   C   H   R   F   K   I   L   K   A   E   C   L   A   M   L   G   R              135
GCC CCT GCC TGC CAT CGA TTC AAA ATT CTC AAA GCA GAA TGT TTA GCA ATG CTT GGT CGA              424

Y   P   E   A   Q   F   V   A   S   G   L   Y   D   C   I   E   K   T   N   A   D          155
TAC CCA GAA GCA CAG TTT GTG GCC AGT GGC CTT TAT GAT TGT ATT GAG AAG ACC AAT GCT GAT          484

A   L   Y   V   R   G   L   C   L   Y   E   D   H   E   K   A   V   C   A   V   Q          175
GCT CTG TAT GTC CGG GGT CTT TGC CTT TAT GAA GAT CAT GAG AAG GCA GTG TGT GCA GTG CAG          544

F   F   V   Q   A   L   R   M   A   P   D   H   E   K   A   C   V   A   C   R              195
TTT TTT GTA CAG GCT CTC AGG ATG GCT CCT GAC CAC GAG AAG GCT TGT GTC GCT TGT AGA              604
```

FIG. 4B

```
N   A   K   A   L   K   A   K   K   E   D   G   N   K   A   F   K   E   G   N
AAT GCC AAA GCC CTT AAA GCC AAG AAG GAA GAT GGG AAT AAA GCC TTT AAG GAA GGA AAT   215
                                                                                  664

Y   K   L   A   Y   E   L   Y   T   E   A   E   L   G   I   D   P   N   N   I   K
TAC AAG CTA GCA TAT GAA CTG TAC ACA GAA GCC TTG GGG ATA GAT CCC AAC AAC ATA AAA   235
                                                                                  724

T   N   A   K   L   Y   C   N   R   G   T   V   S   K   L   R   Q   L   E
ACA AAT GCT AAA CTC TAC TGT AAT CGG GGT ACG GTT AAT TCC AAG CTT AGG CAA CTG GAA   255
                                                                                  784

D   A   I   E   D   C   T   N   A   V   K   L   D   Y   T   I   K   A   Y
GAT GCC ATA GAA GAC TGT ACA AAT GCG GTG AAG CTC GAT GAC ACT TAC AAA GCC TAC       275
                                                                                  844

L   R   R   A   Q   Y   M   D   T   E   Q   F   E   E   A   V   R   D   Y
CTG AGA AGA GCT CAG TGT TAC ATG GAC ACA GAG CAG TTT GAA GAA GCC GTG CGG GAC TAT   295
                                                                                  904

E   K   V   Q   T   E   K   T   K   E   H   K   Q   L   L   K   N   A   Q
GAA AAA GTG TAT CAG ACG GAG AAA ACA AAA GAA CAC AAA CAG CTC CTT AAG AAT GCA CAG   315
                                                                                  964

L   E   L   K   S   K   R   K   D   Y   Y   K   I   L   G   V   D   K   N
CTG GAA CTG AAG AGC AAG AGG AAA GAT TAC TAC AAG ATC CTG GGA GTG GAC AAG AAT       335
                                                                                  1024

A   S   E   D   E   I   K   K   A   Y   R   K   A   L   M   H   P   D
GCC TCT GAG GAC GAG ATC AAG AAG GCC TAC CGG AAA CGG GCC TTG ATG CAC CAT CCA GAT   355
                                                                                  1084

R   H   S   G   A   S   A   E   V   Q   K   E   E   K   F   K   E   V
CGG CAC AGT GGG GCC AGT GCC GAA GTT CAG AAG GAG GAG AAG TTT AAG GAA GTG           375
                                                                                  1144

```
GGA GAG GCC TTT ACC ATC CTC TCT GAT CCC AAG AAA AAG ACT CGT TAT GAC AGT GGA CAG   1204
 D   E   A   F   T   I   L   S   D   P   K   K   K   T   R   Y   D   S   G   Q    415
GAC TTG GAT GAG GAG ATG AAT ATG GGC GAT TTT GAT GCA AAC AAC ATC TTC AAG GCA       1264
 D   L   D   E   E   M   N   M   G   D   F   D   A   N   N   I   F   K   A        435
TTC TTC GGT GGT CCT GGG GGC TTC AGC TTT GAA GCA TCT GGC CCA GGG AAT TTC TAC TTT   1324
 F   F   G   G   P   G   G   F   S   F   E   A   S   G   P   G   N   F   Y   F    439
CAG TTT GGC TAA                                                                   1336
 Q   F   G   *
TGAAGGCCAACTACTTAAAACCCAGAAAATGCAGACTTGCTTGGTTTAACCATGAGTGTGGACAGTTCACTTCCTCCAT   1415
CATGTCCCTGTGTACTTATAGCAGTNTCGTTTTCTCAGTCGGGTGCCCTGTCTGTATGAGGGGTGAAKGAAAGGGGG    1494
CCAGTGCTGAGGACTAGGGAGGGATGGAAGCAGGGTAKACAGGAAGCAGGCAGCTTGTGAATTTTGTGTGTATTGT     1573
TTAACTTTATTAAAAAGAAAAAACAATACTGTAAAWTWTAAAAAGAAAAGRATTAAAAAAAAAAAAAAAAAAAAAA     1652
AAAAAAAAAAAAAAAAAAAAAAAAAAAAAAAAAAAAAAAAAAAAAAAA                                 1700
```

FIG.5A

```
ACGAGCGGGTGACGGCCGGTAGGCTGTAGGCAGCAGAGAGCTGCTGCGGCGGGGGAATCTCCCT    79

GCACCATGAGCCTCGGCTCCGGCCCCGTTAGGGGCCGATAAGCACACAGCGCCCGCCCCCCCATTTGCCCGGGCCCTC   158

GGCTGCGAAGATAGCGGGCCCGGACAGGAAGCTCGAGGAGAAAGCGCTGGGCCCGGTCTCTACGAACACGTGAAGGAAAA   237

GCAGCTCCGTCCACAACGCCGCTTCGGGGCTCCTAGGAGTCGGGCCCCGGCCGTCACCTTCCGGCCGCTGCC   316

M   A   E   D   L   S   A   A   T   S   Y    11
GCTGTCGCCATGCCTTGTTCCCCATCCCCCGCC ATG GCC GAG GAC CTC TCT GCG GCC ACG TCC TAC    384

T   E   D   D   F   Y   C   P   V   C   Q   E   V   L   K   T   P   V   R   T    31
ACC GAA GAT GAT TTC TAC TGC CCC GTC TGT CAG GAG GTG CTC AAA ACG CCC GTG CGG ACC    444

T   A   C   Q   H   V   F   C   R   K   C   F   L   T   A   M   R   E   S   G    51
ACG GCC TGT CAG CAC GTT TTC TGT AGA AAA TGT TTC CTG ACT GCA ATG AGG GAA AGC GGA    504

A   H   C   P   L   C   R   G   N   V   T   R   E   R   A   C   P   E   R    71
GCA CAT TGT CCC CTA TGT CGT GGA AAT GTG ACT AGA AGA GAG AGA GCA TGT CCT GAA CGG    564

A   L   D   L   E   N   I   M   R   K   F   S   G   S   C   R   C   C   A   K    91
GCC TTA GAC CTT GAA AAT ATA ATG AGG AAG TTT TCT GGT AGC TGC AGA TGC TGT GCA AAA    624
```

FIG.5B

```
Q   I   K   F   Y   R   M   R   H   H   Y   K   S   C   K   K   Y   Q   D   E   111
CAG ATT AAA TTC TAT CGC ATG AGA CAT CAT TAC AAA TCT TGT AAG AAG TAT CAG GAT GAA   684

Y   G   V   S   S   I   I   P   N   F   Q   I   S   Q   D   S   V   G   N   S   131
TAT GGT GTT TCT TCT ATC ATT CCA AAC TTT CAG ATC TCT CAA GAT TCA GTA GGG AAC AGC  744

N   R   S   E   T   S   T   S   D   N   T   E   T   Y   Q   E   N   T   S   S   151
AAT AGG AGT GAA ACA TCC ACA TCT GAT AAC ACA GAA ACT TAC CAA GAG AAT ACA AGT TCT  804

S   G   H   P   T   F   K   C   P   L   C   Q   E   S   N   F   T   R   Q   R   171
TCT GGT CAT CCT ACT TTT AAG TGT CCC CTG TGT CAA GAA TCA AAT TTT ACC AGA CAG CGT  864

L   L   D   H   C   N   S   N   N   H   L   F   Q   I   V   P   V   T   C   P   I   191
TTA CTG GAT CAC TGT AAC AGT AAT AAT CAC CTA TTT CAG ATA GTT CCT GTG ACA TGT CCT ATT  924

C   V   S   L   P   W   G   D   P   S   Q   I   T   R   N   F   V   S   H   L   211
TGT GTG TCT CTT CCT TGG GGA GAT CCT AGC CAG ATT ACC AGA AAT TTC GTT AGT CAT CTA  984

N   Q   R   H   Q   F   D   Y   G   E   F   N   L   Q   L   D   E   E   T   231
AAT CAG AGA CAT CAA TTT GAT TAT GGA GAA TTT GTG AAT CTT CAG CTA GAT GAA ACC      1044

Q   Y   Q   T   A   V   E   E   F   F   Q   V   N   I   *                        246
CAA TAC CAA ACT GCT GTT GAA GAA TTT TTT CAA GTA AAC ATT TGA                      1089

AGGCTGTAGACATTTTTGCATTTTGTACCTGCAAGTGCCATCTTTAAGGGGGAAAMTACATGAGTCACCGTTACAGT   1168

AACTTGATGTGTATATTAATAAAGTAATTCAGTCMAAAAAAAAAAAAAAAAAAAAAAAAAAAAAAAAAAAAAAAAAA   1247

```
                                                                                              M   S   E      3
AGTTCACCTACCACCACCTCGGCTCCTGCCGGCCGCCCTCCCGCCGCCACCCTCGCC ATG TCC GAG            74

E   L   S   A   A   T   S   Y   T   E   D   D   F   Y   C   P   V   C   Q   E     23
GAA CTT TCG GCG GCC ACG TCC TAC ACG GAA GAT GAT TTC TAC TGC CCT GTC TGT CAG GAG   134

V   L   K   T   P   V   R   T   A   A   C   Q   H   V   F   C   R   K   C   F     43
GTG CTC AAG ACG CCG GTG CGG ACC GCG GCC TGT CAG CAC GTT TTC TGT AGA AAA TGT TTC   194

L   T   A   M   R   E   S   G   I   H   C   P   L   C   R   G   S   V   T   R     63
CTG ACT GCA ATG AGA GAA AGT GGA ATA CAT TGT CCC CTA TGT CGT GGA AGT GTG ACT AGA   254

R   E   R   A   C   P   E   R   A   L   D   L   E   N   I   M   R   R   H   Y     83
AGA GAA AGA GCA TGT CCG GAA CGG GCC TTA GAT CTT GAA AAT ATC ATG AGA AGG CAT TAC   314

G   S   C   R   C   C   S   K   K   I   K   F   Y   R   M   R   H   H   Y   K    103
GGT AGC TGC AGA TGC TGT TCA AAA AAG ATT AAA TTC TAT CGC ATG AGA CAT CAT TAC AAA   374

S   C   K   Y   Q   D   E   Y   G   V   S   S   E   T   S   A   S   V   P   N    123
TCT TGT AAG TAT CAG GAT GAA TAT GGT GTT TCT TCT GAA ACA TCT GCA TCT GTC CCA AAC   434

S   Q   D   S   V   R   S   S   N   R   S   G   H   P   T   F   K   C   P   L    143
TCT CAA GAT TCA GTA AGG AGC AGT AAT AGG AGT GGG CAT CCT ACC TTT AAG TGT CCC TTA   494

T   Y   Q   E   D   T   S   S   S   R   L   L   D   H   C   N   S   N   H   L    163
ACT TAT CAA GAG GAT ACA AGT TCT TCT CGT TTA GAT CAC TGT AAT AGT AAC CAC CTA TGT   554

E   S   N   F   T   R   Q   R   L   L   D   H   C   N   S   N   H   L   F   Q    183
GAG TCA AAT TTC ACC AGA CAA CGT TTA GAT CAC TGT AAT AGT AAC CAC CTA TTT CAG       614
```

FIG. 6B

```
 I   V   P   V   T   C   P   I   C   V   S   L   P   W   G   D   P   S   Q   I        203
ATA GTT CCT GTG ACA TGT CCT ATT TGT GTG TCT CTT CCT TGG GGA GAT CCT AGC CAG ATT        674

T   R   N   F   V   S   H   L   N   Q   R   H   Q   F   D   Y   G   E   F   V        223
ACT AGA AAT TTC GTT AGT CAT CTA AAT CAA AGA CAT CAG TTT GAT TAT GGA GAA TTT GTG        734

N   L   Q   L   D   E   E   T   Q   Y   Q   T   A   V   E   E   S   F   Q   V        243
AAT CTT CAG CTA GAT GAG GAA ACC CAA TAT CAA ACT GCT GTG GAA GAG TCT TTT CAA GTA        794

N   M   *                                                                             246
AAC ATG TGA                                                                            803

CATGTATAGACACTCTGCCTCCTTGCAACCTACAAGTGCCATCTTTAAGGAGAAGACATGAAGTCACCATTTTCAGTA         882

ATTTGCTGTGCATATTAATAAAAATAATAATTCAGTCTACTGTATTAGGTTTTTAATTGAAAATAAAGGTGGGCCACCC         961

TAATACCATTCTCTAGACAGTTACTTAACAGCATGGAAAGGGTTGTATTCACTGTGTGTGAAAAGAGAATCTCTG            1040

TTGTCTTTTTCTTCCTTGTATTACATATTCTCAATGTTTCATTAAGTTGTTTTTGGTATTTGATATAGTTCCTTCTGTT        1119

TAGTACAGAGATAACAGCAAATTCTGAACGATGTGATTCTTAAAAAGCTAATAAACCTGAGCCATTTGTCAGAGCTGTA        1198

GAATGGAAACTTGAAGTGTTGAAGTGGATAATCCAAAGGGATTTTTTTTGAAGTATAGATTCTAGCTGAGGAATTCAA        1277

CAATAAGAAAGTTGTATTTATGTAATGTTTAGTATTTTTGAAGACTAGTGAGATTTCTTAATAATTTTACTTTGAAA         1356

GCATATTGTACAAATGTTTCTTCTTTTGCTATTAGAAGAACATCAAGAGAAGTTCCTTTGGTGGTTAGTTTGTTATT         1435
```

FIG.6C

```
CAATCTAGGTTGAATAATTTGTAAGCCTAAATGTTATATACCACAGTTCTTGTAGTCAGTATTCTCACTGGGTGATG    1514
AAACTTTTCAGCCAGTGAATGATACATTCAATTAGTTTTTAAAAATCCAAAGTTGCAGATGTATGTGGATATGTACAT   1593
AGACTTTTGCATGTATATATACACATATATCTTTGCCTAGAGTTTGTCAGTTATGTGATATAGAATTTCTATTAAAAAG  1672
TTTTAATAATGGACAAGCAATATAGGATTGAAGTATTTATCTCCTTTGTTTAAATTTGTATGTTACCAAGTTTTTAA    1751
AACAGTAAGCCAAATACTATGTGGTACAGTTGGCTGTTATTACACCTGAAAAATGTAAATGTGCTCACTTGTTACGT    1830
TTGAAAATGATGCATAACTGACGTGTGGTGAGAGATTTACCAGCTACTGTTCACTACATTTAGTCAAACAAAGTT      1909
TGTTCTTAATCTTTGGTATAAGTGTTGTAGAGAAGGCCAAGTCACAAGTAAAGGGTGAAGGGGAATTCTGACATTC     1988
CACACTAACATAACACTGTTATGCTTTCTTAAAATAACTAACCGCAAAGAAAATCTCGAAGTAGTTGCTGCTAAT      2067
ATATACATATATTGTAAAAAAAAAAGTATATTTGATTTTCTGGTAAATCTCG                             2121
```

TUB INTERACTOR (TI) POLYPEPTIDES AND USES THEREFOR

RELATED APPLICATIONS

This application is a divisional application of Ser. No. 08/897,340 filed on Jul. 21, 1997, U.S. Pat. No. 5,955,306, which in turn is a continuation-in-part application of Ser. No. 08/715,032 filed on Sep. 17, 1996, now abandoned. The contents of all of the aforementioned application(s) are incorporated herein by reference.

BACKGROUND OF THE INVENTION

Obesity represents the most prevalent of body weight disorders, and it is the most important nutritional disorder in the western world, with estimates of its prevalence ranging from 30% to 50% within the middle-aged population. Other body weight disorders, such as anorexia nervosa and bulimia nervosa which together affect approximately 0.2% of the female population of the western world, also pose serious health threats. Further, such disorders as anorexia and cachexia (wasting) are also prominent features of other diseases such as cancer, cystic fibrosis, and AIDS.

Obesity, defined as an excess of body fat relative to lean body mass, also contributes to other diseases. For example, this disorder is responsible for increased incidences of diseases such as coronary artery disease, hypertension, stroke diabetes, hyperlipidemia and some cancers. (See, e.g., Nishina, P. M. et al. (1994) Metab. 43:554–558; Grundy, S. M. and Barnett, J. P. (1990) Dis. Mon. 36:641–731) Obesity is not merely a behavioral problem, i.e., the result of voluntary hyperphagia. Rather, the differential body composition observed between obese and normal subjects results from differences in both metabolism and neurologic/metabolic interactions. These differences seem to be, to some extent, due to differences in gene expression, and /or level of gene products or activity (Friedman, J. M. et al.(1991) Mammalian Gene 1:130–144).

The epidemiology of obesity strongly shows that the disorder exhibits inherited characteristics (Stunkard (1990) N. Eng. J. Med. 322:1483). Moll et al. have reported that, in many populations, obesity seems to be controlled by a few genetic loci (Moll et al. (1991) Am. J. Hum. Gen. 49:1243). In addition, human twin studies strongly suggest a substantial genetic basis in the control of body weight, with estimates of heritability of 80–90% (Simopoulos, A. P. and Childs B., eds., 1989, in "Genetic Variation and Nutrition in Obesity", World Review of Nutrition and Diabetes 63, S. Karger, Basel, Switzerland; Borjeson, M., 1976, Acta. Paediatr. Scand. 65:279–287).

Studies of non-obese persons who deliberately attempted to gain weight by systematically over-eating were found to be more resistant to such weight gain and able to maintain an elevated weight only by very high caloric intake. In contrast, spontaneously obese individuals are able to maintain their status with normal or only moderately elevated caloric intake. In addition, it is a commonplace experience in animal husbandry that different strains of swine, cattle, etc., have different predispositions to obesity. Studies of the genetics of human obesity and of models of animal obesity demonstrate that obesity results from complex defective regulation of both food intake, food induced energy expenditure and of the balance between lipid and lean body anabolism.

There are a number of genetic diseases in man and other species which feature obesity among their more prominent symptoms, along with, frequently, dysmorphic features and mental retardation. For example, Prader-Willi syndrome (PWS; reviewed in Knoll, J. H. et al. (1993) Am. J. Med. Genet. 46:2–6) affects approximately 1 in 20,000 live births, and involves poor neonatal muscle tone, facial and genital deformities, and generally obesity.

In addition to PWS, many other pleiotropic syndromes which include obesity as a symptom have been characterized (e.g. Ahlstroem, Carpenter, Bardet-Biedl, Cohen, and Morgagni-Stewart-Monel Syndromes). These syndromes are more genetically straightforward and appear to involve autosomal recessive alleles.

A number of models exist for the study of obesity (see, e.g., Bray, G. A. (1992) Prog. Brain Res. 93:333–341, and Bray, G. A. (1989) Amer. J. Clin. Nutr. 5:891–902). For example, animals having mutations which lead to syndromes that include obesity symptoms have also been identified. Attempts have been made to utilize such animals as models for the study of obesity, and the best studied animal models, to date, for genetic obesity are mice. For reviews, see e.g., Friedman, J. M. et al. (1991) Mamm. Gen. 1:130–144; Friedman, J. M. and Liebel, R. L. (1992) Cell 69:217–220.

Studies utilizing mice have confirmed that obesity is a very complex trait with a high degree of heritability. Mutations at a number of loci have been identified which lead to obese phenotypes. These include the autosomal recessive mutations obese (ob), diabetes (db), fat (fat) and tubby (tub). In addition, the autosomal dominant mutations Yellow at the agouti locus and Adipose (Ad) have been shown to contribute to an obese phenotype.

The ob and db mutations are on chromosomes 6 and 4, respectively, but lead to clinically similar pictures of obesity, evident starting at about one month of age, which include hyperphagia, severe abnormalities in glucose and insulin metabolism, very poor thermoregulation and non-shivering thermogenesis, and extreme torpor and underdevelopment of the lean body mass.

The ob gene and its human homologue have recently been cloned (Zhang, Y. et al., (1994) Nature 372:425–432). The gene appears to produce a 4.5 kb adipose tissue messenger RNA which contains a 167 amino acid open reading frame. The predicted amino acid sequence of the ob gene product indicates that it is a secreted protein and may, therefore, play a role as part of a signaling pathway from adipose tissue which may serve to regulate some aspect of body fat deposition.

The db locus encodes a high affinity receptor for the ob gene product (Chen, H. et al. Cell 84:491–495). The db gene product is a single membrane-spanning receptor most closely related to the gp130 cytokine receptor signal transducing component (Tartaglia, L. A. et al. (1995) Cell 83:1263–1271).

Homozygous mutations at either the fat or tub loci cause obesity which develops more slowly than that observed in ob and db mice (Coleman, D. L., and Eicher, E. M. (1990) J. Heredity 81:424–427), with tub obesity developing slower than that observed in fat animals. This feature of the tub obese phenotype makes the development of tub obese phenotype closest in resemblance to the manner in which obesity develops in humans. Even so, however, the obese phenotype within such animals can be characterized as massive in that animals eventually attain body weights which are nearly two times the average weight seen in normal mice. tub/tub mice develop insulin resistance with their weight gain but do not progress to overt diabetes.

In addition to obesity, retinal defects, hearing loss and infertility have all been observed in tub mice (Heckenlively, 1988, in Retinitis Pigmentosa, Heckenlively, ed., Lippincott, Philadelphia, pp. 221–235; Coleman, D. L. & Eicher, E. M., 1990, J. Hered. 81:424–4a27; Ohlemiller, K. K. et al. (1995) *Neuroreport* 6:845–849). Several human syndromes exist in which such defects are found to co-exist with an obesity phenotype, including Bardet-Biedl syndrome, Ahlstroem syndrome, polycystic ovarian disease and Usher's syndrome.

The fat mutation has been mapped to mouse chromosome 8, while the tub mutation has been mapped to mouse chromosome 7. According to Naggert et al., the fat mutation has recently been identified (Naggert, J. K., et al. (1995) *Nature Genetics* 10:135–141). Specifically, the fat mutation appears to be a mutation within the Cpe locus, which encodes the carboxypeptidase (Cpe) E protein. Cpe is an exopeptidase involved in the processing of prohormones, including proinsulin.

The dominant Yellow mutation at the agouti locus, causes a pleiotropic syndrome which causes moderate adult onset obesity, a yellow coat color, and a high incidence of tumor formation (Herberg, L. and Coleman, D. L. (1977) *Metabolism* 26:59), and an abnormal anatomic distribution of body fat (Coleman, D. L. (1978) *Diabetologia* 14:141–148). This mutation may represent the only known example of a pleiotropic mutation that causes an increase, rather than a decrease, in body size. The mutation causes the widespread expression of a protein which is normally seen only in neonatal skin (Michaud, E. J. et al. (1994) *Genes Devel.* 8:1463–1472).

Other animal models include fa/fa (fatty) rats, which bear many similarities to the ob/ob and db/db mice, discussed above. One difference is that, while fa/fa rats are very sensitive to cold, their capacity for non-shivering thermogenesis is normal. Torpor seems to play a larger part in the maintenance of obesity in fa/fa rats than in the mice mutants. In addition, inbred mouse strains such as NZO mice and Japanese KK mice are moderately obese. Certain hybrid mice, such as the Wellesley mouse, become spontaneously fat. Further, several desert rodents, such as the spiny mouse, do not become obese in their natural habitats, but do become so when fed on standard laboratory feed.

Animals which have been used as models for obesity have also been developed via physical or pharmacological methods. For example, bilateral lesions in the vetromedial hypothalamus (VMH) and ventrolateral hypothalamus (VLH) in the rat are associated, respectively, with hyperphagia and gross obesity and with aphagia, cachexia and anorexia. Further, it has been demonstrated that feeding monosodiumglutamate (MSG) or gold thioglucose to newborn mice also results in an obesity syndrome.

In summary, therefore, obesity, which poses a major, worldwide health problem, represents a highly heritable trait. Given the severity, prevalence and potential heterogeneity of such disorders, there exists a great need for the identification genes involved in the control of body weight.

SUMMARY OF THE INVENTION

The present invention is based on the discovery of novel molecules, referred to herein as "Tub Interactor" ("TI") nucleic acid and polypeptide molecules. Exemplary novel TI molecules are contained in and encoded by: 1) *E. coli* plasmid ptyhq049, which was deposited with the American Type Culture Collection (ATCC) on Aug. 6, 1996 and has been assigned ATCC designation number 98125; 2 *E. coli* plasmid ptyhq054, which was deposited with the American Type Culture Collection (ATCC) on Aug. 6, 1996 and has been assigned ATCC designation number 98126; 3) *E. coli* plasmid ptyhq058, which was deposited with the American Type Culture Collection (ATCC) on Aug. 6, 1996 and has been assigned ATCC designation number 98127; and 4) *E. coli* plasmid ptyhq036, which was deposited with the American Type Culture Collection (ATCC) on Aug. 6, 1996 and has been assigned ATCC designation number 98128.

Six novel TI genes were cloned and identified based on their ability to interact with the C-terminus (i.e. the last 44 amino acids) of htub in a two hybrid assay as further described in the following Examples. hTI-1 (FIG. 1 (SEQ ID NO:1)) is a 1386 base pair nucleic acid encoding a serine protease. hTI-2 (FIG. 2 (SEQ ID NO:2)) is a 2103 base pair nucleic acid containing ANK (i.e. ankyrin) repeats. hTI-3 (FIG. 3 (SEQ ID NO:3)) is a 1048 base pair nucleic acid containing TPR repeats (i.e. tetraticopeptide repeats) and also DNAJ repeats. mTI-3 (FIG. 4 (SEQ ID NO:4)) is a 1700 base pair nucleic acid that is the murine homologue of hTI-3. hTI-4 (FIG. 5 (SEQ ID NO:5)) is a 1421 base pair nucleic acid that contains RING finger repeats and also Zinc finger repeats. mTI-4 (FIG. 6 (SEQ ID NO:6)) is a 2121 base pair nucleic acid that is the murine homologue of hTI-4. A final TI gene (hTI-5) was identified as encoding human serine palmitoyltransferase (GenBank Accession No. U15555).

In one aspect, the invention features isolated vertebrate TI nucleic acid molecules. The disclosed molecules can be non-coding, (e.g. probe, antisense or ribozyme molecules) or can encode a functional TI polypeptide (e.g. a polypeptide which specifically modulates, e.g., by acting as either an agonist or antagonist, at least one bioactivity of the human TI polypeptide). In one embodiment, the nucleic acid molecules can hybridize to the TI gene contained in any of ATCC designation numbers 98125, 98126, 981257, or 98128 or to the complement of the TI gene contained in any of ATCC designation numbers 98125, 98126, 981257, or 98128. In another embodiment, the nucleic acids of the present invention can hybridize to a vertebrate TI gene or to the complement of a vertebrate TI gene. In a further embodiment, the claimed nucleic acid can hybridize with the nucleic acid sequence, designated in SEQ ID NOs:1–6 or to the complement to the nucleic acid sequence designated in SEQ ID NOs:1–6. In a preferred embodiment, the hybridization is conducted under mildly stringent or stringent conditions.

In further embodiments, the nucleic acid molecule is a TI nucleic acid that is at least 70%, preferably 80%, more preferably 85%, and even more preferably at least 90% or 95% homologous in sequence to any of the nucleic acids shown as SEQ ID NOs:1–6 or to the complement of the nucleic acid shown as SEQ ID NOs:1–6. In a further embodiment, the nucleic acid molecule is a TI nucleic acid that is at least 70%, preferably 80%, more preferably 85% and even more preferably at least 90% or 95% similar in sequence to the TI gene contained in any of ATCC designation numbers 98125, 98126, 981257, or 98128 or to the complement of the TI gene contained in any of ATCC designation numbers 98125, 98126, 981257, or 98128.

The invention also provides probes and primers comprising substantially purified oligonucleotides, which correspond to a region of nucleotide sequence which hybridizes to at least 6 consecutive nucleotides of any of the sequences set forth as SEQ ID NOs:1–6 or complements of any of the sequences set forth as SEQ ID NOs:1–6 or naturally occurring mutants thereof. In preferred embodiments, the probe/primer further includes a label group attached thereto, which is capable of being detected.

For expression, the subject nucleic acids can include a transcriptional regulatory sequence, e.g. at least one of a transcriptional promoter (e.g., for constitutive expression or inducible expression) or transcriptional enhancer sequence, which regulatory sequence is operably linked to the gene sequence. Such regulatory sequences in conjunction with a TI nucleic acid molecule can provide a useful vector for gene expression. This invention also describes host cells transfected with said expression vector whether prokaryotic or eukaryotic and in vitro (e.g. cell culture) and in vivo (e.g. transgenic) methods for producing TI proteins by employing said expression vectors.

In another aspect, the invention features isolated TI polypeptides, preferably substantially pure preparations e.g. of plasma purified or recombinantly produced polypeptides. In preferred embodiments, the polypeptide is able to bind to the C-terminus (e.g. the last 44 amino acids) of the human tub protein. In particularly preferred embodiments, the subject polypeptides, whether agonists or antagonists, can suppress the development and/or progression of a weight disorder (obesity, cachexia or anorexia nervosa) or a related disorder (e.g. diabetes).

In a preferred embodiment, the TI polypeptide is encoded by a nucleic acid which hybridizes with any of the nucleic acid sequences represented in SEQ ID NOs:1–6 or with the gene or gene fragment contained in any of ATCC Designation Nos. designation numbers 98125, 98126, 981257, or 98128. The subject TI proteins also include modified protein, which are resistant to post-translational modification, as for example, due to mutations which alter modification sites (such as tyrosine, threonine, serine or aspargine residues), or which prevent glycosylation of the protein, or which prevent interaction of the protein with intracellular proteins involved in signal transduction.

The TI polypeptides can comprise a full length protein or it can comprise a fragment corresponding to one or more particular motifs/domains, or to arbitrary sizes, e.g., at least 5, 10, 25, 50, 100, 150 or 200 amino acids in length. In preferred embodiments, the polypeptide includes a sufficient portion of the domain that interacts with the C-terminus (i.e. the last 44 amino acids) of normal human tub.

Another aspect of the invention features chimeric molecules (e.g. fusion proteins) comprised of a TI protein. For instance, the TI protein can be provided as a recombinant fusion protein which includes a second polypeptide portion, e.g., a second polypeptide having an amino acid sequence unrelated (heterologous) to the TI polypeptide, (e.g. the second polypeptide portion is glutathione-S-transferase, an enzymatic activity such as alkaline phosphatase or an epitope tag).

Yet another aspect of the present invention concerns an immunogen comprising a TI polypeptide in an immunogenic preparation, the immunogen being capable of eliciting an immune response specific for a TI polypeptide; e.g. a humoral response, an antibody response and/or cellular response. In a preferred embodiment, the immunogen comprises an antigenic determinant, e.g. a unique determinant of a protein encoded by any of the nucleic acids SEQ ID NOs:1–6.

A still further aspect of the present invention features antibodies and antibody preparations specifically reactive with an epitope of a TI protein.

The invention also features transgenic non-human animals which include (and preferably express) a heterologous form of a TI gene described herein, or which misexpress an endogenous TI gene (e.g., an animal in which expression of one or more of the subject TI proteins is disrupted). Such a transgenic animal can serve as an animal model for studying cellular and tissue disorders comprising mutated or mis-expressed TI alleles or for use in drug screening. Alternatively, such a transgenic animal can be useful for expressing recombinant TI polypeptides.

In yet another aspect, the invention provides assays, e.g., for screening test compounds to identify modulators (e.g., inhibitors, or alternatively, potentiators) of an interaction between a TI protein and, for example, a tub polypeptide. An exemplary method includes the steps of (i) combining a TI protein or bioactive fragment thereof, a TI protein target molecule (such as Tub), and a test compound, e.g., under conditions wherein, but for the test compound, the TI protein and target molecule are able to interact; and (ii) detecting the formation of a complex which includes the TI protein and the target polypeptide either by directly quantitating the complex, by measuring inductive effects of the TI protein, or, in the instance of a substrate, measuring the conversion to product. A statistically significant change, such as a decrease, in the interaction of the TI protein and target molecule in the presence of a test compound (relative to what is detected in the absence of the test compound) is indicative of a modulation (e.g., inhibition or potentiation of the interaction between the TI protein and the target molecule).

Yet another aspect of the present invention concerns a method for modulating apoptosis in a cell by modulating TI bioactivity, (e.g., by potentiating or disrupting certain protein-protein interactions). In general, whether carried out in vivo, in vitro, or in situ, the method comprises treating the cell with an effective amount of a TI therapeutic so as to alter, relative to the cell in the absence of treatment, lipid uptake by the cell. Accordingly, the method can be carried out with TI modulating agents such as peptide and peptidomimetics or other molecules identified in the above-referenced drug screens which agonize or antagonize the effects of signaling in a biochemical pathway involving a TI protein. Other modulating agents for use as therapeutics include antisense constructs for inhibiting expression of TI proteins, and dominant negative mutants of TI proteins which competitively inhibit ligand interactions upstream and signal transduction downstream of the wild-type TI protein.

A further aspect of the present invention provides a method of determining if a subject is at risk for a disorder characterized by inappropriate TI protein expression, such as, for example, a weight disorder (e.g. obesity, cachexia or anorexia nervosa) or a related disorder, such as diabetes. The method includes detecting, in a tissue of the subject, the presence or absence of a genetic lesion characterized by at least one of (i) a mutation of a gene encoding a TI protein, e.g. represented in any of SEQ ID NOs:1–6 or a homologue thereof; or (ii) the mis-expression of a TI gene. In preferred embodiments, detecting the genetic lesion includes ascertaining the existence of at least one of: a deletion of one or more nucleotides from a TI gene; an addition of one or more nucleotides to the gene, a substitution of one or more nucleotides of the gene, a gross chromosomal rearrangement of the gene; an alteration in the level of a messenger RNA transcript of the gene; the presence of a non-wild type splicing pattern of a messenger RNA transcript of the gene; a non-wild type level of the protein; and/or an aberrant level of soluble TI protein.

For example, detecting the genetic lesion can include (i) providing a probe/primer comprised of an oligonucleotide which hybridizes to a sense or antisense sequence of a TI gene or naturally occurring mutants thereof, or 5' or 3' flanking sequences naturally associated with the TI gene; (ii)

contacting the probe/primer to an appropriate nucleic acid containing sample; and (iii) detecting, by hybridization of the probe/primer to the nucleic acid, the presence or absence of the genetic lesion; e.g. wherein detecting the lesion comprises utilizing the probe/primer to determine the nucleotide sequence of the TI gene and, optionally, of the flanking nucleic acid sequences. For instance, the primer can be employed in a polymerase chain reaction (PCR) or in a ligation chain reaction (LCR). In alternate embodiments, the level of a TI protein is detected in an immunoassay using an antibody which is specifically immunoreactive with the TI protein.

Other features and advantages of the invention will be apparent from the following detailed description and claims.

BRIEF DESCRIPTION OF THE DRAWINGS

FIG. 1 shows the DNA sequence of a novel human TI gene, E. coli plasmid ptyhq049, ATCC designation no. 98125 (hTI-1) (SEQ ID NO:1) and a deduced amino acid sequence.

FIG. 2 shows the DNA sequence of a novel human TI gene, E. coli plasmid ptyhq058, ATCC designation no. 98127 (hTI-2) (SEQ ID NO:2) and a deduced amino acid sequence.

FIG. 3 shows the DNA sequence of a novel human TI gene, E. coli plasmid ptyhq036, ATCC designation no. 98128 (hTI-3) (SEQ ID NO:3) and a deduced amino acid sequence.

FIG. 4 shows the DNA sequence of a novel murine TI gene, E. coli plasmid ptyht101 (mTI-3) (SEQ ID NO:4) and a deduced amino acid sequence.

FIG. 5 shows the DNA sequence of a novel human TI gene, E. coli plasmid ptyhq054, ATCC designation no. 98126 (hTI-4) (SEQ ID NO:5) and a deduced amino acid sequence.

FIG. 6 shows the DNA sequence of a novel murine TI gene, E. coli plasmid ptyht102 (mTI-4) (SEQ ID NO:6) and a deduced amino acid sequence.

DETAILED DESCRIPTION OF THE INVENTION

The present invention is based on the discovery of novel genes, referred to herein as the "Tub interactor" or "TI" genes, which fuction in biochemical pathways involved in weight control and/or related disorder, such as diabetes.

Six novel TI genes were cloned and identified based on their ability to interact with the C-terminus (i.e. the last 44 amino acids) of htub in a two hybrid assay as further described in the following Examples. hTI-1 is a 1386 base pair nucleic acid, the sequence of which is presented in FIG. 1 (SEQ ID NO:1). Based on sequence analysis, the polypeptide encoded by the gene is a putative serine protease.

hTI-2 is a 2103 base pair nucleic acid, the sequence of which is presented in FIG. 2 (SEQ ID NO:2). The sequence contains ANK (i.e. ankyrin) repeats indicating that the protein encoded by the nucleic acid specifically recognize proteins and/or nucleic acid molecules (Michaely, P. and V. Bennett (1992) Trends in Cell Biology 2:127–129). Based on Northern analysis, a major band of 2.4 kb and a minor band of 8 kb corresponding to TI-2 was expressed in all human tissue and cell lines tested. However, the highest expression occurred in the testis, pancreas, liver, uterus and brain.

hTI-3 is a 1048 base pair nucleic acid, the sequence of which is presented in FIG. 3 (SEQ ID NO:3). The sequence contains TPR repeats (i.e. tetraticopeptide repeats) and also DNAJ repeats, indicating that the protein encoded by the nucleic acid is involved in protein-protein interactions. Based on Northern analysis, a major band of 2.2 kb and a minor band of 1.2 kb corresponding to hTI-3 was expressed in all human tissue and cell lines tested. However, the highest expression occurred in skeletal muscle, liver, heart and testis.

mTI-3 is a 1700 base pair nucleic acid, the sequence of which is presented in FIG. 4 (SEQ ID NO:4). A sequence comparison of a 1035 base region indicates that the human and mouse genes are 86.8% identical. Like the human, the murine sequence contains TPR repeats (i.e. tetraticopeptide repeats) (Silkorski, R. J. et al., (Jan. 26, 1990) Cell 60:307–317; Lee, T. G. et al. (April 1994) Mol. Cell. Biol. 14:2331–2342; Barber, G. N et al. (May 1994) Proc. Natl. Acad. Sci. USA 91:4278–4282) and also DNAJ repeats (Silver, P. A. (Jul. 16, 1993) Cell 74:5–6), indicating that the protein encoded by the nucleic acid is involved in protein-protein interactions. Based on Northern analysis, a major band of 1.4 kb corresponding to mTI-3 was expressed in all murine tissue tested (both tub and B6). However, the highest expression occurred in skeletal muscle, liver, heart and testis.

hTI-4 is a 1421 base pair nucleic acid, the sequence of which is presented in FIG. 5 (SEQ ID NO:5). The sequence contains RING finger repeats (Saurin, A. J. et al. (June 1996) TIBS 21:) and also Zinc finger repeats (Lovering R. et al. (March 1993) Proc. Natl. Acad. Sci. USA 90:2112–2116) indicating that the protein encoded by the nucleic acid is involved in nucleic acid (i.e. DNA or RNA) interactions. Based on Northern analysis, bands of 4 and 3 kb corresponding to hTI-4 was expressed in all human tissue and cell lines tested. In addition, a 1.4 kb band was strongly expressed in testis. Further, a band corresponding to 2.4 kb was expressed in the human SHEP, SHSY5Y, SKNMC and SKNSH cell lines.

mTI-4 is a 2121 base pair nucleic acid, the sequence of which is presented in FIG. 6 (SEQ ID NO:6). A sequence comparison of a 959 base region indicates that the human and mouse genes are 86.8% identical. Like the human, the murine sequence contains RING finger repeats and also Zinc finger repeats indicating that the protein encoded by the nucleic acid is involved in nucleic acid (i.e. DNA or RNA) interactions. Based on Northern analysis, major bands of 3.0 and 2.4 kb corresponding to mTI-4 was expressed in all murine tissue tested. In addition, a 1.4 kb band was expressed in Tub and B6 mouse.

Another TI gene (hTI-5) was identified as encoding human serine palmitoyltransferase (GenBank Accession No. U15555), an enzyme that catalyzes the committed step in sphingolipid and ceramide biosythesis. Ceramide is a second messenger that regulates apoptosis via PP2A (Nickels, J. T. and J. R. Broach (1996) Genes & Development 10:382–394.

The cDNAs corresponding to TI gene transcripts were initially cloned from human breast tissue based on the ability of their encoded proteins to bind to the C-tenninal domain (i.e. the last 44 amino acids) of the htub gene product in an assay that detects protein/protein interactions, placing the TI gene products in the same biochemical pathway as tub. The tub protein is described in U.S. patent application Ser. No. 08/631,200 filed on Apr. 12, 1996.

Accordingly, certain aspects of the present invention relate to nucleic acid molecules encoding TI proteins, the TI proteins, antibodies immunoreactive with TI proteins, and preparations of such compositions. in addition, drug discovery assays are provided for identifying agents which can modulate the biological function of TI proteins, such as by altering the interaction of TI molecules with either downstream or upstream elements in the tub signal transduction pathway. Such agents can be useful therapeutically, for example, to modulate weight control and/or diabetes. Moreover, the present invention provides diagnostic and therapeutic assays and reagents for detecting and treating disorders involving, for example, aberrant expression (or loss thereof) of TI genes. Other aspects of the invention are described below or will be apparent to those skilled in the art in light of the present disclosure.

For convenience, the meaning of certain terms and phrases employed in the specification, examples, and appended claims are provided below.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject TI polypeptides with a second amino acid sequence defining a domain (e.g. polypeptide portion) foreign to and not substantially homologous with any domain of one of the TI polypeptides. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula X-TI-Y, wherein TI represents a portion of the protein which is derived from one of the TI proteins, and X and Y are independently absent or represent amino acid sequences which are not related to one of the TI amino acid sequences in an organism, including naturally occurring mutants.

"Complementary" sequences as used herein refer to sequences which have sufficient complementarity to be able to hybridize, forming a stable duplex.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a TI polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

As used herein, the term "gene" or "recombinant gene" refers to a nucleic acid molecule comprising an open reading frame encoding one of the TI polypeptides of the present invention, including both exon and (optionally) intron sequences. A "recombinant gene" refers to nucleic acid molecule encoding a TI polypeptide and comprising TI protein-encoding exon sequences, though it may optionally include intron sequences which are either derived from a chromosomal TI gene or from an unrelated chromosomal gene. Exemplary recombinant genes encoding the subject TI polypeptides are represented in the appended Sequence Listing. The term "intron" refers to a DNA sequence present in a given gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the TI sequences of the present invention.

The term "interact" as used herein is meant to include detectable interactions between molecules, such as can be detected using, for example, a yeast two hybrid assay. The term interact is also meant to include "binding" interactions between molecules. Interactions may be protein-protein or protein-nucleic acid in nature.

The term "isolated" as used herein with respect to nucleic acids, such as DNA or RNA, refers to molecules separated from other DNAs or RNAs, respectively, that are present in the natural source of the macromolecule. For example, an isolated nucleic acid encoding one of the subject TI polypeptides preferably includes no more than 10 kilobases (kb) of nucleic acid sequence which naturally immediately flanks the TI gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "modulation" as used herein refers to both upregulation, i.e., stimulation, and downregulation, i.e. suppression, of a response.

The "non-human animals" of the invention include mammalians such as rodents, non-human primates, sheep, dog, cow, chickens, amphibians, reptiles, etc. Preferred nonhuman animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that one of the recombinant TI genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangably herein when referring to a gene product.

The term "recombinant protein" refers to a polypeptide of the present invention which is produced by recombinant DNA techniques, wherein generally, DNA encoding a TI polypeptide is inserted into a suitable expression vector which is in turn used to transform a host cell to produce the heterologous protein. Moreover, the phrase "derived from", with respect to a recombinant TI gene, is meant to include within the meaning of "recombinant protein" those proteins having an amino acid sequence of a native TI protein, or an amino acid sequence similar thereto which is generated by mutations including substitutions and deletions (including truncation) of a naturally occurring form of the protein.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides of a vertebrate, preferably mammalian, TI gene, such as the TI sequence designated in one of SEQ ID NOs:1–6, or a sequence complementary thereto, or naturally occurring mutants thereof, such that it shows more than 10 times more hybridization, preferably more than 100 times more hybridization, and even more preferably more than 100 times more hybridization than it does to a cellular nucleic acid (e.g., mRNA or genomic DNA) encoding a protein other than a vertebrate, preferably mammalian, TI protein as defined herein.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant TI genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of TI proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a TI polypeptide or, in the case of antisense expression from the transferred gene, the expression of a naturally-occurring form of the TI protein is disrupted.

As used herein, the term "transgene" means a nucleic acid sequence encoding, e.g., one of the TI polypeptides, or an antisense transcript thereto, which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, (e.g. as intron), that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the TI proteins, e.g. either agonistic or antagonistic forms. However, transgenic animals in which the recombinant TI gene is silent are also contemplated, as for example, the FLP or CRE recombinase dependent constructs described below. Moreover, "transgenic animal" also includes those recombinant animals in which gene disruption of one or more TI genes is caused by human intervention, including both recombination and antisense techniques.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Nucleic Acids

As described below, one aspect of the invention pertains to isolated nucleic acids comprising nucleotide sequences encoding Tub interactor or TI polypeptides, and/or equivalents of such nucleic acids. The term equivalent is understood to include nucleotide sequences encoding functionally equivalent TI polypeptides or functionally equivalent peptides having an activity of a TI protein such as described herein. Equivalent nucleotide sequences will include sequences that differ by one or more nucleotide substitution, addition or deletion, such as allelic variants; and will, therefore, include sequences that differ from the nucleotide sequence of the TI gene shown in SEQ ID NOs:1–6 due to the degeneracy of the genetic code.

Preferred nucleic acids are vertebrate TI nucleic acids. Particularly preferred vertebrate TI nucleic acids are mammalian. Regardless of species, particularly preferred TI nucleic acids encode polypeptides that are at least 80% similar to an amino acid sequence of a vertebrate TI protein. In one embodiment, the nucleic acid is a cDNA encoding a polypeptide having at least one bioactivity of the subject TI polypeptide. Preferably, the nucleic acid includes all or a portion of the nucleotide sequence corresponding to the nucleic acid of SEQ ID NOs:1, 3, 5, 7, or 9.

Still other preferred nucleic acids of the present invention encode a TI polypeptide which is comprised of at least 2, 5, 10, 25, 50, 100, 150 or 200 amino acid residues. For example, preferred nucleic acid molecules for use as probes/primer or antisense molecules (i.e. noncoding nucleic acid molecules) can comprise at least about 6, 12, 20, 30, 50, 100, 125, 150 or 200 base pairs in length, whereas coding nucleic acid molecules can comprise about 300, 400, 500, 600, 700, 800, 900, 950, 975, 1000, 1005, 1010 or 1015 base pairs.

Another aspect of the invention provides a nucleic acid which hybridizes under stringent conditions to a nucleic acid represented by one of SEQ ID NOs:1–6. Appropriate stringency conditions which promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a TI nucleic acid of the present invention will bind to one of SEQ ID NOs:1–6 under moderately stringent conditions, for example at about 2.0×SSC and about 40° C. In a particularly preferred embodiment, a TI nucleic acid of the present invention will bind to one of SEQ ID NOs:1–6 under high stringency conditions.

Preferred nucleic acids have a sequence at least 75% homologous and more preferably 80% and even more preferably at least 85% homologous with an amino acid sequence of a TI gene, e.g., such as a sequence shown in one of SEQ ID NOs:1–6. Nucleic acids at least 90%, more preferably 95%, and most preferably at least about 98–99% homologous with a nucleic sequence represented in one of SEQ ID NOs:1–6 are of course also within the scope of the invention. In preferred embodiments, the nucleic acid is mammalian and in particularly preferred embodiments, includes all or a portion of the nucleotide sequence corresponding to the coding region of one of SEQ ID NOs:1–6.

Nucleic acids having a sequence that differs from the nucleotide sequences shown in one of SEQ ID NOs:1–6 due to degeneracy in the genetic code are also within the scope of the invention. Such nucleic acids encode functionally equivalent peptides (i.e., a peptide having a biological activity of a TI polypeptide) but differ in sequence from the sequence shown in the sequence listing due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence of a TI polypeptide. However, it is expected that DNA sequence polymorphisms that do lead to changes in the amino acid sequences of the subject TI polypeptides will exist among mammalians. One skilled in the art will appreciate that these variations in one or more nucleotides (e.g., up to about 3–5% of the nucleotides) of the nucleic acids encoding polypeptides having an activity of a TI polypeptide may exist among individuals of a given species due to natural allelic variation.

As indicated by the examples set out below, TI protein-encoding nucleic acids can be obtained from mRNA present in any of a number of eukaryotic cells. It should also be possible to obtain nucleic acids encoding TI polypeptides of the present invention from genomic DNA from both adults and embryos. For example, a gene encoding a TI protein can be cloned from either a cDNA or a genomic library in accordance with protocols described herein, as well as those generally known to persons skilled in the art. Examples of tissues and/or libraries suitable for isolation of the subject nucleic acids include breast, among others. A cDNA encoding a TI protein can be obtained by isolating total mRNA from a cell, e.g. a vertebrate cell, a mammalian cell, or a human cell, including embryonic cells. Double stranded cDNAs can then be prepared from the total mRNA, and subsequently inserted into a suitable plasmid or bacteriophage vector using any one of a number of known techniques. The gene encoding a TI protein can also be cloned using established polymerase chain reaction techniques in accordance with the nucleotide sequence information provided by the invention. The nucleic acid of the invention can be DNA or RNA or analogs thereof. A preferred nucleic acid is a cDNA represented by a sequence selected from the group consisting of SEQ ID NOs:1–6.

Vectors.

This invention also provides expression vectors containing a nucleic acid encoding a TI polypeptide, operably linked to at least one transcriptional regulatory sequence. "Operably linked" is intended to mean that the nucleotide sequence is linked to a regulatory sequence in a manner which allows expression of the nucleotide sequence. Regulatory sequences are art-recognized and are selected to direct expression of the subject TI proteins. Accordingly, the term "transcriptional regulatory sequence" includes promoters, enhancers and other expression control elements. Such regulatory sequences are described in Goeddel; *Gene Expression Technology: Methods in Enzymology* 185, Academic Press, San Diego, Calif. (1990). In one embodiment, the expression vector includes a recombinant gene encoding a peptide having an agonistic activity of a subject TI polypeptide, or alternatively, encoding a peptide which is an antagonistic form of the TI protein. Such expression vectors can be used to transfect cells and thereby produce polypeptides, including fusion proteins, encoded by nucleic acids as described herein. Moreover, the gene constructs of the present invention can also be used as a part of a gene therapy protocol to deliver nucleic acids encoding either an agonistic or antagonistic form of one of the subject TI proteins. Thus, another aspect of the invention features expression vectors for in vivo or in vitro transfection and expression of a TI polypeptide in particular cell types so as to reconstitute the function of, or alternatively, abrogate the function of TI-induced signaling in a tissue. This could be desirable, for example, when the naturally-occurring form of the protein is misexpressed; or to deliver a form of the protein which alters differentiation of tissue. Expression vectors may also be employed to inhibit neoplastic transformation.

In addition to viral transfer methods, such as those illustrated above, non-viral methods can also be employed to cause expression of a subject TI polypeptide in the tissue of an animal. Most nonviral methods of gene transfer rely on normal mechanisms used by mammalian cells for the uptake and intracellular transport of macromolecules. In preferred embodiments, non-viral targeting means of the present invention rely on endocytic pathways for the uptake of the subject TI polypeptide gene by the targeted cell. Exemplary targeting means of this type include liposomal derived systems, poly-lysine conjugates, and artificial viral envelopes.

Probes and Primers

Moreover, the nucleotide sequences determined from the cloning of TI genes from mammalian organisms will further allow for the generation of probes and primers designed for use in identifying and/or cloning TI homologues in other cell types, e.g. from other tissues, as well as TI homologues from other mammalian organisms. For instance, the present invention also provides a probe/primer comprising a substantially purified oligonucleotide, which oligonucleotide comprises a region of nucleotide sequence that hybridizes under stringent conditions to at least approximately 12, preferably 25, more preferably 40, 50 or 75 consecutive nucleotides of sense or anti-sense sequence selected from the group consisting of SEQ ID NOs:1–6 or naturally occurring mutants thereof. For instance, primers based on the nucleic acid represented in SEQ ID NOs:1, 3, 5, 7 or 9 can be used in PCR reactions to clone TI homologues. Preferred primers for hTI-4 are set forth as SEQ ID NOs:9 and 10. Preferred primers for mTI-3 are set forth as SEQ ID NOs:13 and 14. Preferred primers for hTI-3 are set forth in SEQ ID NOs:17 and 18. Preferred primers for hTI-1 are set forth in SEQ ID NOs:21 and 22. Preferred primers for mTI-4 are set forth in SEQ ID NOs:25 and 26. Preferred primers for hTI-2 are set forth in SEQ ID NOs:29 and 30.

Likewise, probes based on the subject TI sequences can be used to detect transcripts or genomic sequences encoding the same or homologous proteins. In preferred embodiments, the probe further comprises a label group attached thereto and able to be detected, e.g. the label group is a radioisotope, a fluorescent compound, an enzyme, or an enzyme co-factor.

As discussed in more detail below, such probes can also be used as a part of a diagnostic test kit for identifying cells or tissue which misexpress a TI protein, such as by measuring a level of a TI-encoding nucleic acid in a sample of cells from a patient; e.g. detecting TI mRNA levels or determining whether a genomic TI gene has been mutated or deleted. Briefly, nucleotide probes can be generated from the subject TI genes which facilitate histological screening of intact tissue and tissue samples for the presence (or absence) of TI-encoding transcripts. Similar to the diagnostic uses of anti-TI antibodies, the use of probes directed to TI messages, or to genomic TI sequences, can be used for both predictive and therapeutic evaluation of allelic mutations which might be manifest in, for example, a predisposition to diabetes. Used in conjunction with immunoassays as described herein, the oligonucleotide probes can help facilitate the determination of the molecular basis for a disorder which may involve some abnormality associated with expression (or lack thereof) of a TI protein. For instance, variation in polypeptide synthesis can be differentiated from a mutation in a coding sequence.

Antisense, Ribozyme and Triplex Techniques

Another aspect of the invention relates to the use of the isolated nucleic acid in "antisense" therapy. As used herein, "antisense" therapy refers to administration or in situ generation of oligonucleotide molecules or their derivatives which specifically hybridize (e.g. bind) under cellular conditions, with the cellular mRNA and/or genomic DNA encoding one or more of the subject TI proteins so as to inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a TI protein. Alternatively, the antisense construct is an oligonucleotide probe which is generated ex vivo and which, when introduced into the cell causes inhibition of expression by hybridizing with the mRNA and/or genomic sequences of a TI gene. Such oligonucleotide probes are preferably modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668. With respect to antisense DNA, oligodeoxyribonucleotides derived from the translation initiation site, e.g., between the −10 and +10 regions ofthe TI nucleotide sequence of interest, are preferred. Particularly preferred antisense molecules are set forth in SEQ ID NOs:11, 15, 19, 23 and 27.

Antisense approaches involve the design of oligonucleotides (either DNA or RNA) that are complementary to TI mRNA. The antisense oligonucleotides will bind to the TI mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. (1994) *Nature* 372:333). Therefore, oligonucleotides complementary to either the 5' or 3' untranslated, non-coding regions of a TI gene could be used in an antisense approach to inhibit translation of endogenous TI mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of TI mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. the oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. U.S.A.* 86:6553–6556; Lemaitre et al. (1987) *Proc. Natl. Acad. Sci. USA* 84:648–652; PCT Publication No. WO 88/09810, published Dec. 15, 1988) or the blood-brain barrier (see, e.g., PCT Publication No. WO 89/10134, published Apr. 25, 1988), hybridization-triggered cleavage agents. (See, e.g., Krol et al. (1988) *BioTechniques* 6:958–976) or intercalating agents. (See, e.g., Zon (1988) *Pharm. Res.* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxyethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al. (1987) *Nucl. Acids Res.* 15:6625–6641). The oligonucleotide is a 2'-0-methylribonucleotide (Inoue et al. (1987) *Nucl. Acids Res.* 15:6131–6148), or a chimeric RNA-DNA analogue (Inoue et al. (1987) *FEBS Lett.* 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988) *Nucl. Acids Res.* 16:3209), methylphosphonate oligonucleotides can be prepared by use of controlled pore glass polymer supports (Sarin et al. (1988) *Proc. Natl. Acad. Sci. U.S.A.* 85:7448–7451), etc.

While antisense nucleotides complementary to the TI coding region sequence can be used, those complementary to the transcribed untranslated region are most preferred. For example, an antisense oligonucleotide as set forth in SEQ ID NOs:11, 15, 19, 23 and 27 can be utilized in accordance with the invention.

The antisense molecules should be delivered to cells which express TI in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it is often difficult to achieve intracellular concentrations of the antisense sufficient to suppress translation on endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous TI transcripts and thereby prevent translation of the TI mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon (1981) *Nature* 290:304–310), the promoter contained in the 3' long terminal repeat of Rous sarcoma virus (Yamamoto et al. (1980) *Cell* 22:787–797), the herpes thymidine kinase promoter (Wagner et al. (1981) *Proc. Natl. Acad. Sci. U.S.A.* 78:1441–1445), the regulatory sequences of the metallothionein gene (Brinster et al. (1982) *Nature* 296:39–42), etc. Any type of plasmid, cosmid, YAC or viral vector can be used to prepare the recombinant DNA construct which can be introduced directly into the tissue site; e.g., the choroid plexus or hypothalamus. Alternatively, viral vectors can be used which selectively infect the desired tissue; (e.g., for brain, herpesvirus vectors may be used), in which case administration may be accomplished by another route (e.g., systematically).

Ribozyme molecules designed to catalytically cleave TI mRNA transcripts can also be used to prevent translation of TI mRNA and expression of TI (See, e.g., PCT Publication No. WO 90/11364, published Oct. 4, 1990; Sarver et al. (1990) *Science* 247:1222–1225 and U.S. Pat. No. 5,093, 246). While ribozymes that cleave mRNA at site specific recognition sequences can be used to destroy TI mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) *Nature* 334:585–591. There are hundreds of potential hammerhead ribozyme cleavage sites within the nucleotide sequence of human TI cDNA (FIG. 1). Preferably the ribozyme is engineered so that the cleavage recognition site is located near the 5' end of the TI mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug, et al. (1984) *Science* 224:574–578; Zaug and Cech (1986) *Science* 231:470–475; Zaug, et al. (1986) *Nature* 324:429–433; published PCT Publication No. WO 88/04300 by University Patents Inc.; Been and Cech, (1986) *Cell* 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a TI gene. Particularly preferred ribozymes are set forth in SEQ ID NOs:8, 12, 16, 20, 24 and 28.

As in the antisense approach, the ribozymes can be composed of modified oligonucleotides (e.g. for improved stability, targeting, etc.) and should be delivered to cells which express the TI gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous TI messages and inhibit translation. Because ribozymes unlike antisense molecules, are catalytic, a lower intracellular concentration is required for efficiency.

Endogenous TI gene expression can also be reduced by inactivating or "knocking out" the TI gene or its promoter using targeted homologous recombination. (see, e.g., Smithies et al. (1985) *Nature* 317:230–234; Thomas and Capecchi (1987) *Cell* 51:503–512; Thompson et al. (1989) *Cell* 5:313–321; each of which is incorporated by reference herein in its entirety). For example, a mutant, non-functional TI (or a completely unrelated DNA sequence) flanked by DNA homologous to the endogenous TI gene (either the coding regions or regulatory regions of the TI gene) can be used, with or without a selectable marker and/or a negative selectable marker, to transfect cells that express TI in vivo. Insertion of the DNA construct, via targeted homologous recombination, results in inactivation of the TI gene. Such approaches are particularly suited in the agricultural field where modifications to ES (embryonic stem) cells can be used to generate animal offspring with an inactive TI (e.g., see Thomas and Capecchi, 1987, and Thompson, 1989, supra). However this approach can be adapted for use in humans provided the recombinant DNA constructs are directly administered or targeted to the required site in vivo using appropriate viral vectors, e.g., herpes virus vectors for delivery to brain tissue; e.g., the hypothalamus and/or choroid plexus.

Alternatively, endogenous TI gene expression can be reduced by targeting deoxyribonucleotide sequences complementary to the regulatory region of the TI gene (i.e., the TI promoter and/or enhancers) to form triple helical structures that prevent transcription of the TI gene in target cells in the body. (See generally, Helene, C. (1991) *Anticancer Drug Des.* 6(6):569–84; Helene, C., et al. (1992) *Ann. N.Y. Acad. Sci.* 660:27–36; and Maher, L. J. (1992) *Bioassays* 14(12):807–15).

Likewise, the antisense constructs of the present invention, by antagonizing the normal biological activity of one of the TI proteins, can be used in the manipulation of issue, e.g. lipid metabolism, both in vivo and for ex vivo tissue cultures.

Furthermore, like the antisense techniques (e.g. microinjection of antisense molecules, or transfection with plasmids whose transcripts are antisense with regard to a TI mRNA or gene sequence) antagonizing the normal biological activity of one of the TI proteins can be used to investigate role of TI in lipid metabolism. Such techniques can be utilized in cell culture, but can also be used in the creation of transgenic animals, as detailed below.

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'–3', 3'–5' manner, such that they base pair with first one strand of a duplex and then the other, eliminating the necessity for a sizable stretch of either purines or pyrimidines to be present on one strand of a duplex.

Antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Polypeptides of the Invention

The present invention also makes available isolated TI polypeptides which are isolated from, or otherwise substantially free of other cellular proteins, especially other signal transduction factors and/or transcription factors which may normally be associated with the TI polypeptide. The term "substantially free of other cellular proteins" (also referred to herein as "contaminating proteins") or "substantially pure or purified preparations" are defined as encompassing preparations of TI polypeptides having less than about 20% (by dry weight) contaminating protein, and preferably having less than about 5% contaminating protein. Functional forms of the subject polypeptides can be prepared, for the first time, as purified preparations by using a cloned gene as described herein. By "purified", it is meant, when referring to a peptide or DNA or RNA sequence, that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" and "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions. In preferred embodiments, purified TI preparations will lack any contaminating proteins from the same animal from which TI is normally produced, as can be accomplished by recombinant expression of, for example, a human TI protein in a non-human cell.

Full length proteins or fragments corresponding to one or more particular motifs and/or domains or to arbitrary sizes, for example, at least 5, 10, 25, 50, 75, 100, 125, 150 amino acids in length are within the scope of the present invention.

For example, isolated TI polypeptides can be encoded by all or a portion of a nucleic acid sequence shown in any of SEQ ID NOs:1–6. Isolated peptidyl portions of TI proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a TI polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") TI protein.

Another aspect of the present invention concerns recombinant forms of the TI proteins. Recombinant polypeptides preferred by the present invention, in addition to native TI proteins, are encoded by a nucleic acid, which is at least 85% homologous and more preferably 90% homologous and most preferably 95% homologous with an amino acid sequence represented by SEQ ID NOs:1–6. Polypeptides which are encoded by a nucleic acid that is at least about 98–99% homologous with the sequence of SEQ ID NOs: 1–6 are also within the scope of the invention. In a preferred embodiment, a TI protein of the present invention is a mammalian TI protein. In a particularly preferred embodiment a TI protein is encoded by one of the nucleic acids set forth as SEQ ID NOs:1–6. In particularly preferred embodiment, a TI protein has a TI bioactivity. It will be understood that certain post-translational modifications, e.g., phosphorylation and the like, can increase the apparent molecular weight of the TI protein relative to the unmodified polypeptide chain.

The present invention further pertains to recombinant forms of one of the subject TI polypeptides. Such recombinant TI polypeptides preferably are capable of functioning in one of either role of an agonist or antagonist of at least one biological activity of a wildtype ("authentic") TI protein of the appended sequence listing. The term "evolutionarily related to", with respect to amino acid sequences of TI proteins, refers to both polypeptides having amino acid sequences which have arisen naturally, and also to mutational variants of human TI polypeptides which are derived, for example, by combinatorial mutagenesis.

In general, polypeptides referred to herein as having an activity (e.g., are "bioactive") of a TI protein are defined as polypeptides which include an amino acid sequence encoded by all or a portion of the nucleic acid sequences shown in one of SEQ ID NOs:1–6 and which mimic or antagonize all or a portion of the biological/biochemical activities of a naturally occurring TI protein. In preferred embodiments a TI protein of the present invention specifically interacts with a the carboxy terminus (i.e. last 44 amino acids) of the human tub polypeptide. Examples of such biological activity include the ability to modulate weight control/or diabetes. Other biological activities of the subject TI proteins are described herein or will be reasonably apparent to those skilled in the art. According to the present invention, a polypeptide has biological activity if it is a specific agonist or antagonist of a naturally-occurring form of a TI protein.

The present invention further pertains to methods of producing the subject TI polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed and the protein isolated. A cell culture includes host cells, media and other byproducts. Suitable media for cell culture are well known in the art. The recombinant TI polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant TI polypeptide is a fusion protein containing a domain which facilitates its purification, such as GST fusion protein.

Moreover, it will be generally appreciated that, under certain circumstances, it may be advantageous to provide homologues of one of the subject TI polypeptides which function in a limited capacity as one of either a TI agonist (mimetic) or a TI antagonist, in order to promote or inhibit only a subset of the biological activities of the naturally-occurring form of the protein. Thus, specific biological effects can be elicited by treatment with a homologue of limited function, and with fewer side effects relative to treatment with agonists or antagonists which are directed to all of the biological activities of naturally occurring forms of TI proteins.

Homologues of each of the subject TI proteins can be generated by mutagenesis, such as by discrete point mutation(s), or by truncation. For instance, mutation can give rise to homologues which retain substantially the same, or merely a subset, of the biological activity of the TI polypeptide from which it was derived. Alternatively, antagonistic forms of the protein can be generated which are able to inhibit the function of the naturally occurring form of the protein, such as by competitively binding to a downstream or upstream member of the TI cascade which includes the TI protein. In addition, agonistic forms of the protein may be generated which are constitutively active. Thus, the TI protein and homologues thereof provided by the subject invention may be either positive or negative regulators of weight control and/or diabetes.

The recombinant TI polypeptides of the present invention also include homologues of the wild-type TI proteins, such as versions of those protein which are resistant to proteolytic cleavage, as for example, due to mutations which alter ubiquitination or other enzymatic targeting associated with the protein.

TI polypeptides may also be chemically modified to create TI derivatives by forming covalent or aggregate conjugates with other chemical moieties, such as glycosyl groups, lipids, phosphate, acetyl groups and the like. Covalent derivatives of TI proteins can be prepared by linking the chemical moieties to functional groups on amino acid sidechains of the protein or at the N-terminus or at the C-terminus of the polypeptide.

Modification of the structure of the subject TI polypeptides can be for such purposes as enhancing therapeutic or prophylactic efficacy, stability (e.g., ex vivo shelf life and resistance to proteolytic degradation in vivo), or post-translational modifications (e.g., to alter phosphorylation pattern of protein). Such modified peptides, when designed to retain at least one activity of the naturally-occurring form of the protein, or to produce specific antagonists thereof, are considered functional equivalents of the TI polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, *Biochemistry*, 2nd ed., Ed. by L. Stryer, W. H. Freeman and Co., 1981). Whether a change in the amino acid sequence of a peptide results in a functional TI homologue (e.g. finctional in the sense that the resulting polypeptide mimics or antagonizes the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject TI proteins as well as truncation mutants, and is especially useful for identifying potential variant sequences (e.g. homologues) that are functional in modulating signal transduction from a lipid receptor. The purpose of screening such combinatorial libraries is to generate, for example, novel TI homologues which can act as either agonists or antagonist, or alternatively, possess novel activities all together. To illustrate, TI homologues can be engineered by the present method to provide selective, constitutive activation of a tub signaling pathway. Thus, combinatorially-derived homologues can be generated to have an increased potency relative to a naturally occurring form of the protein.

Likewise, TI homologues can be generated by the present combinatorial approach to selectively inhibit (antagonize) induction by a lipid. For instance, mutagenesis can provide TI homologues which are able to bind other signal pathway proteins (or DNA) yet prevent propagation of the signal, e.g. the homologues can be dominant negative mutants. Moreover, manipulation of certain domains of TI by the present method can provide domains more suitable for use in fusion proteins.

In one embodiment, the variegated library of TI variants is generated by combinatorial mutagenesis at the nucleic acid level, and is encoded by a variegated gene library. For example, a mixture of synthetic oligonucleotides can be enzymatically ligated into gene sequences such that the degenerate set of potential TI sequences are expressible as individual polypeptides, or alternatively, as a set of larger fusion proteins (e.g. for phage display) containing the set of TI sequences therein.

There are many ways by which such libraries of potential TI homologues can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential TI sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *Proc. Natl. Acad. Sci. USA* 89:2429–2433; Devlin et al. (1990) *Science* 249: 404–406; Cwirla et al. (1990) *Proc. Natl. Acad. Sci. USA* 87: 6378–6382; as well as U.S. Pat. Nos. 5,223,409, 5,198,346, and 5,096,815).

Likewise, a library of coding sequence fragments can be provided for a TI clone in order to generate a variegated population of TI fragments for screening and subsequent selection of bioactive fragments. A variety of techniques are known in the art for generating such libraries, including chemical synthesis. In one embodiment, a library of coding sequence fragments can be generated by (i) treating a double stranded PCR fragment of a TI coding sequence with a nuclease under conditions wherein nicking occurs only about once per molecule; (ii) denaturing the double stranded DNA; (iii) renaturing the DNA to form double stranded DNA which can include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of TI homologues. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate TI sequences created by combinatorial mutagenesis techniques.

In one embodiment, cell based assays can be exploited to analyze the variegated TI library. For instance, the library of expression vectors can be transfected into a cell line ordinarily responsive to insulin. The transfected cells are then contacted with the insulin and the effect of the TI mutant on signaling by a Y5 receptor can be detected. Plasmid DNA can then be recovered from the cells which score for inhibition, or alternatively, potentiation of lipid receptor induction, and the individual clones further characterized.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, a new technique has been developed recently, recrusive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan (1992) *Proc. Natl. Acad. Sci. USA* 89:7811–7815; Yourvan et al. (1992) *Parallel Problem Solving from Nature*, 2., In Maenner and Manderick, eds., Elsevier Publishing Co., Amsterdam, pp. 401–410; Delgrave et al. (1993) *Protein Engineering* 6(3):327–331).

The invention also provides for reduction of the TI proteins to generate mimetics, e.g. peptide or non-peptide agents, which are able to disrupt binding of a TI polypeptide of the present invention with either upstream or downstream components of a lipid uptake signaling cascade, such as binding proteins or interactors. Thus, such mutagenic techniques as described above are also useful to map the determinants of the TI proteins which participate in protein-protein interactions involved in, for example, binding of the subject TI polypeptide to proteins which may function upstream (including both activators and repressors of its activity) or to proteins or nucleic acids which may function downstream of the TI polypeptide, whether they are positively or negatively regulated by it, for example. To illustrate, the critical residues of a subject TI polypeptide which are involved in molecular recognition of, for example, tub or other components upstream or downstream of a TI can be determined and used to generate TI-derived peptidomimetics which competitively inhibit binding of the authentic TI protein with that moiety. By employing, for example, scanning mutagenesis to map the amino acid residues of each of the subject TI proteins which are involved in binding other extracellular proteins, peptidomimetic compounds can be generated which mimic those residues of the TI protein which facilitate the interaction. Such mimetics may then be used to interfere with the normal function of a TI protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J. Med. Chem.* 29:295; and Ewenson et al. in *Peptides: Structure and Function* (Proceedings of the 9th American Peptide Symposium) Pierce Chemical Co. Rockland, Ill., 1985), b-turn dipeptide cores (Nagai et al. (1985) *Tetrahedron Lett* 26:647; and Sato et al. (1986) *J. Chem. Soc. Perkin. Trans.* 1:1231), and b-aminoalcohols (Gordon et al. (1985) *Biochem. Biophys. Res. Commun.* 126:419; and Dann et al. (1986) *Biochem. Biophys. Res. Commun.* 134:71).

Cells Expressing Recombinant TI Polypeptides.

This invention also pertains to host cells transfected to express a recombinant form of the subject TI polypeptides. The host cell may be any prokaryotic or eukaryotic cell. Thus, a nucleotide sequence derived from the cloning of mammalian TI proteins, encoding all or a selected portion of the full-length protein, can be used to produce a recombinant form of a TI polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins, e.g. MAP kinase, p53, WT1, PTP phosphatases, SRC, and the like. Similar procedures, or modifications thereof, can be employed to prepare recombinant TI polypeptides by microbial means or tissue-culture technology in accord with the subject invention.

The recombinant TI genes can be produced by ligating a nucleic acid encoding a TI protein, or a portion thereof, into a vector suitable for expression in either prokaryotic cells, eukaryotic cells, or both. Expression vectors for production of recombinant forms of the subject TI polypeptides include plasmids and other vectors. For instance, suitable vectors for the expression of a TI polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, a TI polypeptide is produced recombinantly utilizing an expression vector generated by sub-cloning the coding sequence of one of the TI genes represented in SEQ ID NOs:1, 3, 5, 7, or 9.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, PKO-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant TI polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a TI protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *Proc. Natl. Acad Sci.* 84:2718–1722). Therefore, removal of an N-terminal methionine, if desired, can be achieved either in vivo by expressing TI-derived polypeptides in a host which produces MAP (e.g., *E. coli* or CM89 or *S. cerevisiae*), or in vitro by use of purified MAP (e.g., procedure of Miller et al., supra).

In other embodiments transgenic animals, described in more detail below could be used to produce recombinant proteins.

Fusion Proteins and Immunogens.

In another embodiment, the coding sequences for the polypeptide can be incorporated as a part of a fusion gene including a nucleotide sequence encoding a different polypeptide. This type of expression system can be useful under conditions where it is desirable to produce an immunogenic fragment of a TI protein. For example, the VP6 capsid protein of rotavirus can be used as an immunologic carrier protein for portions of the TI polypeptide, either in the monomeric form or in the form of a viral particle. The nucleic acid sequences corresponding to the portion of a subject TI protein to which antibodies are to be raised can be incorporated into a fusion gene construct which includes coding sequences for a late vaccinia virus structural protein to produce a set of recombinant viruses expressing fusion proteins comprising TI epitopes as part of the virion. It has been demonstrated with the use of immunogenic fusion proteins utilizing the hepatitis b surface antigen fusion proteins that recombinant hepatitis b virions can be utilized in this role as well. Similarly, chimeric constructs coding for fusion proteins containing a portion of a TI protein and the poliovirus capsid protein can be created to enhance immunogenicity of the set of polypeptide antigens (see, for example, EP Publication No: 0259149; and Evans et al. (1989) *Nature* 339:385; Huang et al. (1988) *J. Virol.* 62:3855; and Schlienger et al. (1992) *J. Virol.* 66:2).

The Multiple Antigen Peptide system for peptide-based immunization can also be utilized to generate an immunogen, wherein a desired portion of a TI polypeptide is obtained directly from organo-chemical synthesis of the peptide onto an oligomeric branching lysine core (see, for example, Posnett et al. (1988) *J. Biol. Chem.* 263:1719 and Nardelli et al. (1992) *J. Immunol.* 148:914). Antigenic determinants of TI proteins can also be expressed and presented by bacterial cells.

In addition to utilizing fusion proteins to enhance immunogenicity, it is widely appreciated that fusion proteins can also facilitate the expression of proteins, and accordingly, can be used in the expression of the TI polypeptides of the present invention. For example, TI polypeptides can be generated as glutathione-S-transferase (GST-fusion) proteins. Such GST-fusion proteins can enable easy purification of the TI polypeptide, as for example by the use of glutathione-derivatized matrices (see, for example, *Current Protocols in Molecular Biology*, eds. Ausubel et al. (John Wiley & Sons, NY 1991)).

In another embodiment, a fusion gene coding for a purification leader sequence, such as a poly-(His)/ enterokinase cleavage site sequence at the N-terminus of the desired portion of the recombinant protein, can allow purification of the expressed fusion protein by affinity chromatography using a Ni2+ metal resin. The purification leader sequence can then be subsequently removed by treatment with enterokinase to provide the purified protein (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Antibodies

Another aspect of the invention pertains to an antibody specifically reactive with a mammalian TI protein. For example, by using immunogens derived from a TI protein, e.g. based on the cDNA sequences, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., a mammalian TI polypeptide or an antigenic fragment which is capable of eliciting an antibody response, or a fusion protein as described above). Techniques for conferring immunogenicity on a protein or peptide include conjugation to carriers or other techniques well known in the art. An immunogenic portion of a TI protein can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immunospecific for antigenic determinants of a TI protein of a mammal, e.g. antigenic determinants of a protein encoded by SEQ ID NOs:1–6 or closely related homologues (e.g. at least 90% homologous, and more preferably at least 94% homologous).

Following immunization of an animal with an antigenic preparation of a TI polypeptide, anti-TI antisera can be obtained and, if desired, polyclonal anti-TI antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature* 256: 495–497), the human B cell hybridoma technique (Kozbar et al. (1983) *Immunology Today* 4:72), and the EBV-hybridoma technique to produce human monoclonal antibodies (Cole et al., (1985) *Monoclonal Antibodies and Cancer Therapy*, Alan R. Liss, Inc. pp. 77–96). Hybridoma cells can be screened immunochemically for production of antibodies specifically reactive with a mammalian TI polypeptide of the present invention and monoclonal antibodies isolated from a culture comprising such hybridoma cells. In one embodiment anti-human TI antibodies specifically react with any of the proteins encoded by the DNA of ATCC deposit Nos. 98125–98128.

The term "antibody" as used herein is intended to include fragments thereof which are also specifically reactive with one of the subject mammalian TI polypeptides. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain and chimeric molecules having affinity for a TI protein conferred by at least one CDR region of the antibody. In preferred embodiments, the antibody further comprises a label attached thereto and able to be detected, (e.g. the label can be a radioisotope, fluorescent compound, enzyme or enzyme co-factor).

Antibodies which specifically bind TI epitopes can also be used in immunohistochemical staining of tissue samples in order to evaluate the abundance and pattern of expression of each of the subject TI polypeptides. Anti-TI antibodies can be used diagnostically in immuno-precipitation and immuno-blotting to detect and evaluate TI protein levels in tissue as part of a clinical testing procedure. For instance, such measurements can be useful in predictive valuations of the onset or progression of proliferative disorders. Likewise, the ability to monitor TI protein levels in an individual can allow determination of the efficacy of a given treatment regimen for an individual afflicted with such a disorder. The level of TI polypeptides may be measured from cells in bodily fluid, such as in samples of cerebral spinal fluid, such as produced by biopsy. Diagnostic assays using anti-TI antibodies can include, for example, immunoassays designed to aid in early diagnosis of a degenerative disorder. Diagnostic assays using anti-TI polypeptide antibodies can also include immunoassays designed to aid in early diagnosis and phenotyping neoplasic or hyperplastic disorders.

Another application of anti-TI antibodies of the present invention is in the immunological screening of cDNA libraries constructed in expression vectors such as λ gt11, λgt18–23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a TI protein, e.g. other orthologues of a particular TI protein or other paralogues from the same species, can then be detected with antibodies, as, for example, reacting nitrocellulose filters lifted from infected plates with anti-TI antibodies. Positive phage detected by this assay can then be isolated from the infected plate. Thus, the presence of TI homologues can be detected and cloned from other animals, as can alternate isoforms (including splicing variants) from humans.

Methods of Treating Disease

There are a wide variety of disorders for which TI molecules of the present invention can be used in treatment. As discussed herein TI molecule can increase the transcription or activity of TI molecules in a cell. A TI molecule therapeutic can be, as appropriate, any of the preparations described above, including isolated polypeptides, gene therapy constructs, antisense molecules, peptidomimetics or agents identified in the drug assays provided herein.

In preferred embodiments the subject TI molecules are modulated to control weight in a subject. Hypothalamic neuropeptide Y (NPY) is a member of the pancreatic polypeptide family and is a potent feeding signal. NPY levels in the paraventricular nucleus (PVN) of the brain have been shown to increase with food deprivation and return to normal after insulin injections (Sahu et al. (1995) *Endocrinology* 136:5718). In one embodiment the subject TI molecules are modulated to control weight in a subject by modulation of a biochemical pathway involving NPY. NPY is thought to signal via the Y5 receptor (Gerald et al. (1996) *Nature* 382:168). The distribution of Y5 mRNA shows that the Y5 receptor is also involved in regulating the emotional aspect of appetitive behaviors. In another embodiment the subject TI molecules are modulated to control weight by modulation of a biochemical pathway involving the Y5 receptor.

Insulin regulates food intake by altering NPY expression in the hypothalamus of the brain (Schwartz et al. (1992) *Endocr Rev.* 13:387). Insulin deficiency, which can be caused, for example, by diabetes, is thought to lead to increased NPY expression in the hypothalamus and to the hyperphagia characteristic of uncontrolled type I diabetes (Sipols et al. (1995) *Diabetes* 44:147). In one embodiment the subject TI molecules are modulated to control weight in a subject by modulation of a biochemical pathway involving insulin. In another embodiment, obesity is controlled by modulation of a biochemical pathway involving insulin-like growth factor II (IGF-II).

In other embodiments, the subject TI molecules are modulated to affect a bioactivity of tub in order to effect a treatment for weight control. In a preferred embodiment the subject TI molecules are modulated to control obesity, diabetes, or cachexia.

In still other embodiments, the subject TI molecules are modulated to control apoptosis in a cell. Apoptosis, or programmed cell death, is characterized by distinct morphological changes and can be triggered by a variety of mechanisms. Certain apoptosis-inducing agents stimulate sphingomyelinases, which act on sphingolipids resulting in the generation of phosphocholine and ceramide, a key regulator of cell cycle control and apoptosis (Pushkareva et al. (1995) *Immunology Today* 16:295). Ceramide is thought to act as a second messenger since a soluble analog of ceramide mimics the affects of agents that induce ceramide production (Law and Rossie (1995) *J. Biol Chem.* 270:12808). Ceramide is thought to control apoptosis via its interaction with the protein phosphatase 2A (PP2A) family of serine/threonine protein phosphatases (Hannun (1994) *J. Biol. Chem.* 269:3125). The catalytic subunit of PP-2A has been shown to be activated by Ceramide (Law and Rossie, supra).

In a preferred embodiment the subject TI molecules are modulated to control apoptosis in a cell of the PVN of the brain. In one embodiment modulation of the molecules to control apoptosis in the PVN of the brain leads to one or more of weight control and diabetes in a subject.

In one embodiment apoptosis is modulated by modulating the activity of TI-1 in a cell. In yet another embodiment apoptosis is modulated by modulating the activity of TI-2 in a cell. In still another embodiment apoptosis is modulated by modulating the activity of TI-3 in a cell. In another embodiment apoptosis is modulated by modulating TI-4 activity in a cell. In addition, therapy may involve modulation of any combination of the disclosed TI molecules.

The present invention will also be useful in treating neurodegenerative diseases which are characterized by apoptosis, including Alzheimer's disease, Parkinson's disease, Huntington's chorea, amylotrophic lateral sclerosis and the like, as well as spinocerebellar degenerations.

In another embodiment the present invention can be used to modulate a pathway involving integrin-mediated signaling.

In another embodiment the subject TI molecules are modulated to control cell cycle progression. Entry of cells into mitosis characteristically involves coordinated and simultaneous events, which include, for example, cytoskeletal rearrangements, disassembly of the nuclear envelope and of the nucleoli, and condensation of chromatin into chromosomes. Cell-cycle events are thought to be regulated by a series of interdependent biochemical steps, with the initiation of late events requiring the successful completion of those proceeding them. In eukaryotic cells mitosis does not normally take place until the G1, S and G2 phases of the cell-cycle are completed. For instance, at least two stages in the cell cycle are regulated in response to DNA damage, the G1/S and the G2/M transitions. These transitions serve as checkpoints to which cells delay cell-cycle progress to allow repair of damage before entering either S phase, when damage would be perpetuated, or M phase, when breaks would result in loss of genomic material. Both the G1/S and G2/M checkpoints are known to be under genetic control as there are mutants that abolish arrest or delay which ordinarily occur in wild-type cells in response to DNA damage.

Tumor suppressors have also been linked to cell cycle control. For example, both p53 (Green (1989) *Cell* 56:1–3; Mowat et al (1985) *Nature* 314:633–636) and the retinoblastoma gene produce (Rb) have been linked to cell cycle control. The first firm evidence for a specific biochemical link between p53 and the cell cycle comes a finding that p53 apparently regulates expression of a second protein, p21, which inhibits cyclin-dependent kinases (cdks) needed to drive cells through the cell cycle, e.g. from G1 into S phase (Xiong et al. (1993) *Nature* 366:701–704). C6 ceramide has been shown to cause dephosphorylation of Rb and Rb deficient cells are more resistant to ceramide-induced growth suppression (Pushkareva et al. supra).

In one embodiment cell cycle progression is modulated by modulating the activity of TI-1 in a cell. In yet another embodiment cell cycle progression is modulated by modulating the activity of TI-2 in a cell. In still another embodiment cell cycle progression is modulated by modulating the activity of TI-3 in a cell. In another embodiment cell cycle progression is modulated by modulating TI-4 in a cell. In addition, therapy may involve modulation of any combination of the disclosed TI molecules.

Since, in some cases, genes may be upregulated in a disease state and in other cases may be suppressed, it will be desirable to activate and/or potentiate or suppress and/or downmodulate TI bioactivity depending on the condition to be treated using the techniques compounds and methods described herein.

Among the approaches which may be used to ameliorate disease symptoms involving the misexpression of a TI gene are, for example, anti sense, ribozyme, and triple helix molecules described above. Compounds that compete with an TI protein for binding to upstream or downstream elements in a lipid uptake signaling cascade will antagonize a TI protein, thereby inducing a therapeutic effect. Examples of suitable compounds include the antagonists or homologues described in detail above. In other instances, the increased expression or bioactivity of a TI protein may be desirable and may be accomplished by, for example the use of the TI agonists or mimetics or by gene replacement therapy, as described herein.

Compounds identified as increasing or decreasing TI gene expression or protein activity can be administered to a subject at therapeutically effective dose to treat the diseases described herein. A therapeutically effective dose refers to that amount of the compound sufficient to effect a change in a TI-associated disorder, such as abnormal weight control and/or diabetes.

Effective Dose

Toxicity and therapeutic efficacy of such compounds can be determined by standard pharmaceutical procedures in cell cultures or experimental animals, e.g., for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Formulation and Use

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the oligomers of the invention can be formulated for a variety of loads of administration, including systemic and topical or localized administration. Techniques and formulations generally may be found in *Remmington's Pharmaceutical Sciences*, Meade Publishing Co., Easton, Pa. For systemic administration, injection is preferred, including intramuscular, intravenous, intraperitoneal, and subcutaneous. For injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art.

In clinical settings, the gene delivery systems for the therapeutic TI gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) *Proc. Natl. Acad Sci. USA* 91: 3054–3057). A TI gene, such as any one of the sequences represented in the group consisting of SEQ ID NOs:1–6 or a sequence homologous thereto can be delivered in a gene therapy construct by electroporation using techniques described, for example, by Dev et al. ((1994) *Cancer Treat. Rev.* 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Diagnostic and Prognostic Assays

In the diagnostic and prognostic assays described herein, in addition to the TI nucleic acid molecules and polypeptides described above, the present invention provides for the use of a nucleic acid comprising at least a portion of a TI nucleic acid molecule, for example, at least a portion of a nucleic acid sequence shown in SEQ ID NOs:1–6 or polypeptides encoded by at least a portion of the nucleic acid sequence shown in SEQ ID NOs:1–6.

The present method provides a method for determining if a subject is at risk for a disorder characterized by apoptosis or aberrant cell proliferation. In preferred embodiments, the methods can be characterized as comprising detecting, in a sample of cells from the subject, the presence or absence of a genetic lesion characterized by at least one of (i) an alteration affecting the integrity of a gene encoding a TI-protein, or (ii) the mis-expression of the TI gene. To illustrate, such genetic lesions can be detected by ascertaining the existence of at least one of (i) a deletion of one or more nucleotides from a TI gene, (ii) an addition of one or more nucleotides to a TI gene, (iii) a substitution of one or more nucleotides of a TI gene, (iv) a gross chromosomal rearrangement of a TI gene, (v) a gross alteration in the level of a messenger RNA transcript of a TI gene, (vii) aberrant modification of a TI gene, such as of the methylation pattern of the genomic DNA, (vii) the presence of a non-wild type splicing pattern of a messenger RNA transcript of a TI gene, (viii) a non-wild type level of a TI-protein, (ix) allelic loss of a TI gene, and (x) inappropriate post-translational modification of a TI-protein. As set out below, the present invention provides a large number of assay techniques for detecting lesions in a TI gene, and importantly, provides the ability to discern between different molecular causes underlying TI-dependent aberrant cell growth, proliferation and/or differentiation.

In an exemplary embodiment, there is provided a nucleic acid composition comprising a (purified) oligonucleotide probe including a region of nucleotide sequence which is capable of hybridizing to a sense or antisense sequence of a TI gene, such as represented by any of SEQ ID NOs:1–6, or naturally occurring mutants thereof, or 5' or 3' flanking sequences or intronic sequences naturally associated with the subject TI genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels.

As set out above, one aspect of the present invention relates to diagnostic assays for determining, in the context of cells isolated from a patient, if mutations have arisen in one or more TI of the sample cells. The present method provides a method for determining if a subject is at risk for a disorder characterized by aberrant cell proliferation and/or differentiation. In preferred embodiments, the method can be generally characterized as comprising detecting, in a sample of cells from the subject, the presence or absence of a genetic lesion characterized by an alteration affecting the integrity of a gene encoding a TI. To illustrate, such genetic lesions can be detected by ascertaining the existence of at least one of (i) a deletion of one or more nucleotides from a TI-gene, (ii) an addition of one or more nucleotides to a TI-gene, (iii) a substitution of one or more nucleotides of a TI-gene, and (iv) the presence of a non-wild type splicing pattern of a messenger RNA transcript of a TI-gene. As set out below, the present invention provides a large number of assay techniques for detecting lesions in TI genes.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the TI-gene (see Abravaya et al. (1995) *Nuc Acid Res* 23:675–682). In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to a TI gene under conditions such that hybridization and amplification of the TI-gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Another embodiment of the invention provides for a nucleic acid composition comprising a (purified) oligonucleotide probe including a region of nucleotide sequence which is capable of hybridizing to a sense or antisense sequence of a TI-gene, or naturally occurring mutants thereof, or 5' or 3' flanking sequences or intronic sequences naturally associated with the subject TI-genes or naturally occurring mutants thereof. The nucleic acid of a cell is rendered accessible for hybridization, the probe is exposed to nucleic acid of the sample, and the hybridization of the probe to the sample nucleic acid is detected. Such techniques can be used to detect lesions at either the genomic or mRNA level, including deletions, substitutions, etc., as well as to determine mRNA transcript levels. Such oligonucleotide probes can be used for both predictive and therapeutic evaluation of allelic mutations which might be manifest in, for example, apoptosis or aberrant cell growth.

The methods described herein may be performed. for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a TI gene.

Antibodies directed against wild type or mutant TI proteins, which are discussed, above, may also be used in disease diagnostics and prognostics. Such diagnostic methods, may be used to detect abnormalities in the level of TI protein expression, or abnormalities in the structure and/or tissue, cellular, or subcellular location of TI protein. Structural differences may include, for example, differences in the size, electronegativity, or antigenicity of the mutant TI protein relative to the normal TI protein. Protein from the tissue or cell type to be analyzed may easily be detected or isolated using techniques which are well known to one of skill in the art, including but not limited to western blot analysis. For a detailed explanation of methods for carrying out western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of TI proteins. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the TI protein, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an anti-TI protein specific antibody is via linkage to an enzyme and use in an enzyme immunoassay (EIA) (Voller, "The Enzyme Linked Immunosorbent Assay (ELISA)", *Diagnostic Horizons* 2:1–7, 1978, Microbiological Associates Quarterly Publication, Walkersville, Md.; Voller, et al., J. Clin. Pathol. 31:507–520 (1978); Butler, Meth. Enzymol. 73:482–523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a TI gene or gene product can be used to monitor the course of treatment or therapy.

Drug Screening Assays

In drug screening assays described herein, in addition to the TI nucleic acid molecules and polypeptides described above, the present invention also provides for the use of nucleic acid molecules comprising at least a portion of a TI nucleic acid molecule, for example, at least a portion of a sequence shown in SEQ ID NOs:1–6 or polypeptides encoded by at least a portion of the nucleic acid sequence shown in any of SEQ ID NOs:1–6.

Furthermore, by making available purified and recombinant TI polypeptides, the present invention facilitates the development of assays which can be used to screen for drugs, including homologues, which are either agonists or antagonists of the normal cellular function of the subject polypeptides. In one embodiment, the assay evaluates the ability of a compound to modulate binding between a TI polypeptide and a molecule, be it protein or DNA, that interacts either upstream or downstream of the TI polypeptide in a lipid transfer pathway. A variety of assay formats will suffice and, in light of the present inventions, will be comprehended by a skilled artisan.

Cell-Free Assays

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements. Accordingly, in an exemplary screening assay of the present invention, the compound of interest is contacted with proteins which may function upstream (including both activators and repressors of its activity) or to proteins or nucleic acids which may function downstream of the TI polypeptide, whether they are positively or negatively regulated by it. To the mixture of the compound and the upstream or downstream element is then added a composition containing a TI polypeptide. Detection and quantification of complexes of TI with it's upstream or downstream elements provide a means for determining a compound's efficacy at inhibiting (or potentiating) complex formation between TI and the TI-binding elements. The efficacy of the compound can be assessed by generating dose response curves from data obtained using various concentrations of the test compound. Moreover, a control assay can also be performed to provide a baseline for comparison. In the control assay, isolated and purified TI polypeptide is added to a composition containing the TI-binding element, and the formation of a complex is quantitated in the absence of the test compound.

Complex formation between the TI polypeptide and a binding element (e.g., Tub) may be detected by a variety of techniques. Modulation of the formation of complexes can be quantitated using, for example, detectably labeled proteins such as radiolabeled, fluorescently labeled, or enzymatically labeled TI polypeptides, by immunoassay, or by chromatographic detection.

Typically, it will be desirable to immobilize either TI or its binding protein to facilitate separation of complexes from uncomplexed forms of one or both of the proteins, as well as to accommodate automation of the assay. Binding of TI to an upstream or downstream element, in the presence and absence of a candidate agent, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/TI (GST/TI) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of TI-binding protein found in the bead fraction quantitated from the gel using standard electrophoretic techniques such as described in the appended examples.

Other techniques for immobilizing proteins on matrices are also available for use in the subject assay. For instance, either TI or its cognate binding protein can be immobilized utilizing conjugation of biotin and streptavidin. For instance, biotinylated TI molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with TI but which do not interfere with binding of upstream or downstream elements can be derivatized to the wells of the plate, and TI trapped in the wells by antibody conjugation. As above, preparations of a TI-binding protein and a test compound are incubated in the TI-presenting wells of the plate, and the amount of complex trapped in the well can be quantitated. Exemplary methods for detecting such complexes, in addition to those described above for the GST-immobilized complexes, include immunodetection of complexes using antibodies reactive with the TI binding element, or which are reactive with TI protein and compete with the binding element; as well as enzyme-linked assays which rely on detecting an enzymatic activity associated with the binding element, either intrinsic or extrinsic activity. In the instance of the latter, the enzyme can be chemically conjugated or provided as a fusion protein with the TI binding protein. To illustrate, the TI binding protein can be chemically cross-linked or genetically fused with horseradish peroxidase, and the amount of polypeptide trapped in the complex can be assessed with a chromogenic substrate of the enzyme, e.g. 3,3'-diamino-benzadine tetrahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) *J. Biol. Chem.* 249:7130).

For processes which rely on immunodetection for quantitating one of the proteins trapped in the complex, antibodies against the protein, such as anti-TI antibodies, can be used. Alternatively, the protein to be detected in the complex can be "epitope tagged" in the form of a fusion protein which includes, in addition to the TI sequence, a second polypeptide for which antibodies are readily available (e.g. from commercial sources). For instance, the GST fusion proteins described above can also be used for quantification of binding using antibodies against the GST moiety. Other useful epitope tags include mycepitopes (e.g., see Ellison et al. (1991) *J. Biol. Chem.* 266:21150–21157) which includes a 10-residue sequence from c-myc, as well as the pFLAG system (International Biotechnologies, Inc.) or the pEZZ-protein A system (Pharmacia, N.J.).

Cell Based Assays

In addition to cell-free assays, such as described above, the readily available TI proteins provided by the present invention also facilitates the generation of cell-based assays for identifying small molecule agonists/antagonists and the like. For example, cells which are sensitive to apoptosis can be caused to overexpress a recombinant TI protein in the presence and absence of a test agent of interest, with the assay scoring for modulation in TI responses by the target cell mediated by the test agent. As with the cell-free assays, agents which produce a statistically significant change in TI-dependent responses (either inhibition or potentiation) can be identified. In an illustrative embodiment, the expression or activity of a TI is modulated in embryos or cells and the effects of compounds of interest on the readout of interest (such as apoptosis) are measured. For example, the expression of genes which are up- or down-regulated in response to a TI-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected.

Further, the transgenic animals described herein may be used to generate cell lines, containing one or more cell types involved in a weight disorder, that can be used as cell culture models for diseases or disorders described herein. While primary cultures derived from transgenic animals of the invention may be utilized, the generation of continuous cell lines is preferred. For examples of techniques which may be used to derive a continuous cell line from the transgenic animals, see Small et al. (1985) *Mol. Cell Biol.* 5:642–648.

In the event that the TI proteins themselves, or in complexes with other proteins, are capable of binding DNA and modifying transcription of a gene, a transcriptional based assay could be used, for example, in which a TI-responsive regulatory sequence is operably linked to a detectable marker gene.

Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject TI polypeptides can be used to generate a "two hybrid" assay (see, for example, U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and PCT Publication No. WO 94/10300), for isolating coding sequences for other cellular proteins which bind to or interact with TI, such as the C-terminus of tub, and the like. Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for a TI polypeptide. The second hybrid protein encodes a transcriptional activation domain fused in frame to a sample gene from a cDNA library. If the bait and sample hybrid proteins are able to interact, e.g., form a TI-dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the TI and sample proteins. The use of the subject TI molecules in a three hybrid assay which allows for phosphorylation of the assay components, such as for example by the inclusion of src, or the PDGF cytoplasmic domain is also provided for.

Transgenic Animals

These systems may be used in a variety of applications. For example, the cell- and animal-based model systems may be used to further characterize TI genes and proteins. In addition, such assays may be utilized as part of screening strategies designed to identify compounds which are capable of ameliorating disease symptoms. Thus, the animal- and cell-based models may be used to identify drugs, pharmaceuticals, therapies and interventions which may be effective in treating disease.

Animal-Based Systems

One aspect of the present invention concerns transgenic animals which are comprised of cells (of that animal) which contain a transgene of the present invention and which preferably (though optionally) express an exogenous TI protein in one or more cells in the animal. A TI transgene can encode the wild-type form of the protein, or can encode homologues thereof, including both agonists and antagonists, as well as antisense constructs. In preferred embodiments, the expression of the transgene is restricted to specific subsets of cells, tissues or developmental stages utilizing, for example, cis-acting sequences that control expression in the desired pattern. In the present invention, such mosaic expression of a TI protein can be essential for many forms of lineage analysis and can additionally provide a means to assess the effects of, for example, lack of TI expression which might grossly alter development in small patches of tissue within an otherwise normal embryo. Toward this and, tissue-specific regulatory sequences and conditional regulatory sequences can be used to control expression of the transgene in certain spatial patterns. Moreover, temporal patterns of expression can be provided by, for example, conditional recombination systems or prokaryotic transcriptional regulatory sequences.

Genetic techniques which allow for the expression of transgenes can be regulated via site-specific genetic manipulation in vivo are known to those skilled in the art. For instance, genetic systems are available which allow for the regulated expression of a recombinase that catalyzes the genetic recombination a target sequence. As used herein, the phrase "target sequence" refers to a nucleotide sequence that is genetically recombined by a recombinase. The target sequence is flanked by recombinase recognition sequences and is generally either excised or inverted in cells expressing recombinase activity. Recombinase catalyzed recombination events can be designed such that recombination of the target sequence results in either the activation or repression of expression of one of the subject TI proteins. For example, excision of a target sequence which interferes with the expression of a recombinant TI gene, such as one which encodes an antagonistic homologue or an antisense transcript, can be designed to activate expression of that gene. This interference with expression of the protein can result from a variety of mechanisms, such as spatial separation of the TI gene from the promoter element or an internal stop codon. Moreover, the transgene can be made wherein the coding sequence of the gene is flanked by recombinase recognition sequences and is initially transfected into cells in a 3' to 5' orientation with respect to the promoter element. In such an instance, inversion of the target sequence will reorient the subject gene by placing the 5' end of the coding sequence in an orientation with respect to the promoter element which allow for promoter driven transcriptional activation.

The transgenic animals of the present invention all include within a plurality of their cells a transgene of the present invention, which transgene alters the phenotype of the "host cell" with respect to regulation of cell growth, death and/or differentiation. Since it is possible to produce transgenic organisms of the invention utilizing one or more of the transgene constructs described herein, a general description will be given of the production of transgenic organisms by referring generally to exogenous genetic material. This general description can be adapted by those skilled in the art in order to incorporate specific transgene sequences into organisms utilizing the methods and materials described below.

In an illustrative embodiment, either the cre/loxP recombinase system of bacteriophage P1 (Lakso et al. (1992) *Proc. Natl. Acad. Sci. USA* 89:6232–6236; Orban et al. (1992) *Proc. Natl. Acad. Sci. USA* 89:6861–6865) or the FLP recombinase system of *Saccharomyces cerevisiae* (O'Gorman et al. (1991) *Science* 251:1351–1355; PCT Publication No. WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J. Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation expression of a recombinant TI protein can be regulated via control of recombinase expression.

Use of the cre/loxP recombinase system to regulate expression of a recombinant TI protein requires the construction of a transgenic animal containing transgenes encoding both the Cre recombinase and the subject protein. Animals containing both the Cre recombinase and a recombinant TI gene can be provided through the construction of "double" transgenic animals. A convenient method for providing such animals is to mate two transgenic animals each containing a transgene, e.g., a TI gene and recombinase gene.

One advantage derived from initially constructing transgenic animals containing a TI transgene in a recombinase-mediated expressible format derives from the likelihood that the subject protein, whether agonistic or antagonistic, can be deleterious upon expression in the transgenic animal. In such an instance, a founder population, in which the subject transgene is silent in all tissues, can be propagated and maintained. Individuals of this founder population can be crossed with animals expressing the recombinase in, for example, one or more tissues and/or a desired temporal pattern. Thus, the creation of a founder population in which, for example, an antagonistic TI transgene is silent will allow the study of progeny from that founder in which disruption of TI mediated induction in a particular tissue or at certain developmental stages would result in, for example, a lethal phenotype.

Similar conditional transgenes can be provided using prokaryotic promoter sequences which require prokaryotic proteins to be simultaneously expressed in order to facilitate expression of the TI transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the trans-activating protein, e.g. a recombinase or a prokaryotic protein, is delivered to the tissue and caused to be expressed, such as in a cell-type specific manner. By this method, a TI transgene could remain silent into adulthood until "turned on" by the introduction of the trans-activator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with H-2$^b$, H-2$^d$ or H-2$^q$ haplotypes such as C57BL/6 or DBA/1. The line(s) used to practice this invention may themselves be transgenics, and/or may be knockouts (i.e., obtained from animals which have one or more genes partially or completely suppressed).

In one embodiment, the transgene construct is introduced into a single stage embryo. The zygote is the best target for micro-injection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *Proc. Natl. Acad. Sci. USA* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material. As set out above, the exogenous genetic material will, in certain embodiments, be a DNA sequence which results in the production of a TI protein (either agonistic or antagonistic), and antisense transcript, or a TI mutant. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) Proc. Natl. Acad. Sci USA 73:1260–1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) Proc. Natl. Acad. Sci. 82:6927–6931; Van der Putten et al. (1985) Proc. Natl. Acad. Sci. USA 82:6148–6152). Transfection is easily and efficiently obtained by culturing the blastomeres on a monolayer of virus-producing cells (Van der Putten, supra; Stewart et al. (1987) EMBO J. 6:383–388). Alternatively, infection can be performed at a later stage. Virus or virus-producing cells can be injected into the blastocoele (Jahner et al. (1982) Nature 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al., supra).

A third type of target cell for transgene introduction is the embryonal stem cell (ES). ES cells are obtained from pre-implantation embryos cultured in vitro and fused with embryos (Evans et al. (1981) Nature 292:154–156; Bradley et al. (1984) Nature 309:255–258; Gossler et al. (1986) Proc. Natl. Acad. Sci. USA 83:9065–9069; and Robertson et al. (1986) Nature 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468–1474.

In one embodiment, gene targeting, which is a method of using homologous recombination to modify an animal's genome, can be used to introduce changes into cultured embryonic stem cells. By targeting a TI gene of interest in ES cells, these changes can be introduced into the germlines of animals to generate chimeras. The gene targeting procedure is accomplished by introducing into tissue culture cells a DNA targeting construct that includes a segment homologous to a target TI locus, and which also includes an intended sequence modification to the TI genomic sequence (e.g., insertion, deletion, point mutation). The treated cells are then screened for accurate targeting to identify and isolate those which have been properly targeted.

Gene targeting in embryonic stem cells is in fact a scheme contemplated by the present invention as a means for disrupting a TI gene function through the use of a targeting transgene construct designed to undergo homologous recombination with one or more TI genomic sequences. The targeting construct can be arranged so that, upon recombination with an element of a TI gene, a positive selection marker is inserted into (or replaces) coding sequences of the targeted gene. The inserted sequence functionally disrupts the TI gene, while also providing a positive selection trait. Exemplary TI targeting constructs are described in more detail below.

Generally, the embryonic stem cells (ES cells) used to produce the knockout animals will be of the same species as the knockout animal to be generated. Thus for example, mouse embryonic stem cells will usually be used for generation of knockout mice.

Embryonic stem cells are generated and maintained using methods well known to the skilled artisan such as those described by Doetschman et al. (1985) J. Embryol. Exp. Morphol. 87:27–45). Any line of ES cells can be used, however, the line chosen is typically selected for the ability of the cells to integrate into and become part of the germ line of a developing embryo so as to create germ line transmission of the knockout construct. Thus, any ES cell line that is believed to have this capability is suitable for use herein. One mouse strain that is typically used for production of ES cells, is the 129J strain. Another ES cell line is murine cell line D3 (American Type Culture Collection, catalog no. CKL 1934) Still another preferred ES cell line is the WW6 cell line (Ioffe et al. (1995) Proc. Natl. Acad. Sci. USA 92:7357–7361). The cells are cultured and prepared for knockout construct insertion using methods well known to the skilled artisan, such as those set forth by Robertson in: Teratocarcinomas and Embryonic Stem Cells: A Practical Approach, E. J. Robertson, ed. IRL Press, Washington, D.C., 1987); by Bradley et al. (1986) Current Topics in Devel. Biol. 20:357–371); and by Hogan et al. (Manipulating the Mouse Embryo: A Laboratory Manual, Cold Spring Harbor Laboratory Press, Cold Spring Harbor, N.Y., 1986).

Insertion of the knockout construct into the ES cells can be accomplished using a variety of methods well known in the art including for example, electroporation, microinjection, and calcium phosphate treatment. A preferred method of insertion is electroporation.

Each knockout construct to be inserted into the cell must first be in the linear form. Therefore, if the knockout construct has been inserted into a vector (described infra), linearization is accomplished by digesting the DNA with a suitable restriction endonuclease selected to cut only within the vector sequence and not within the knockout construct sequence.

For insertion, the knockout construct is added to the ES cells under appropriate conditions for the insertion method chosen, as is known to the skilled artisan. Where more than one construct is to be introduced into the ES cell, each knockout construct can be introduced simultaneously or one at a time.

If the ES cells are to be electroporated, the ES cells and knockout construct DNA are exposed to an electric pulse using an electroporation machine and following the manufacturer's guidelines for use. After electroporation, the ES cells are typically allowed to recover under suitable incubation conditions. The cells are then screened for the presence of the knockout construct.

Screening can be accomplished using a variety of methods. Where the marker gene is an antibiotic resistance gene, for example, the ES cells may be cultured in the presence of an otherwise lethal concentration of antibiotic. Those ES cells that survive have presumably integrated the knockout construct. If the marker gene is other than an antibiotic resistance gene, a Southern blot of the ES cell genomic DNA can be probed with a sequence of DNA designed to hybridize only to the marker sequence. Alternatively, PCR can be used. Finally, if the marker gene is a gene that encodes an enzyme whose activity can be detected (e.g., b-galactosidase), the enzyme substrate can be added to the cells under suitable conditions, and the enzymatic activity can be analyzed. One skilled in the art will be familiar with other useful markers and the means for detecting their presence in a given cell. All such markers are contemplated as being included within the scope of the teaching of this invention.

The knockout construct may integrate into several locations in the ES cell genome, and may integrate into a different location in each ES cell's genome due to the occurrence of random insertion events. The desired location of insertion is in a complementary position to the DNA sequence to be knocked out, e.g., the TI coding sequence, transcriptional regulatory sequence, etc. Typically, less than about 1–5% of the ES cells that take up the knockout construct will actually integrate the knockout construct in the desired location. To identify those ES cells with proper integration of the knockout construct, total DNA can be extracted from the ES cells using standard methods. The DNA can then be probed on a Southern blot with a probe or probes designed to hybridize in a specific pattern to genomic DNA digested with particular restriction enzyme(s). Alternatively, or additionally, the genomic DNA can be amplified by PCR with probes specifically designed to amplify DNA fragments of a particular size and sequence (i.e., only those cells containing the knockout construct in the proper position will generate DNA fragments of the proper size).

After suitable ES cells containing the knockout construct in the proper location have been identified, the cells can be inserted into an embryo. Insertion may be accomplished in a variety of ways known to the skilled artisan, however a preferred method is by microinjection. For microinjection, about 10–30 cells are collected into a micropipette and injected into embryos that are at the proper stage of development to permit integration of the foreign ES cell containing the knockout construct into the developing embryo. For instance, as the appended Examples describe, the transformed ES cells can be microinjected into blastocysts.

The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan, and are set forth by, e.g., Bradley et al. (supra).

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the knockout construct by looking for mosaic coat color (indicating that the ES cell was incorporated into the developing embryo). Thus, for example, if the ES cell line carries the genes for white fur, the embryo selected will carry genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the knockout construct using Southern blots and/or PCR as described above. Offspring that appear to be mosaics may then be crossed to each other, if they are believed to carry the knockout construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the knockout offspring are available. For example, Northern blots can be used to probe the mRNA for the presence or absence of transcripts encoding either the gene knocked out, the marker gene, or both. In addition, Western blots can be used to assess the level of expression of the TI gene knocked out in various tissues of the offspring by probing the Western blot with an antibody against the particular TI protein, or an antibody against the marker gene product, where this gene is expressed. Finally, in situ analysis (such as fixing the cells and labeling with antibody) and/or FACS (fluorescence activated cell sorting) analysis of various cells from the offspring can be conducted using suitable antibodies to look for the presence or absence of the knockout construct gene product.

Yet other methods of making knock-out or disruption transgenic animals are also generally known. See, for example, Manipulating the Mouse Embryo, (Cold Spring Harbor Laboratory Press, Cold Spring Harbor, N.Y., 1986). Recombinase dependent knockouts can also be generated, e.g. by homologous recombination to insert target sequences, such that tissue specific and/or temporal control of inactivation of a TI-gene can be controlled by recombinase sequences (described infra).

Animals containing more than one knockout construct and/or more than one transgene expression construct are prepared in any of several ways. The preferred manner of preparation is to generate a series of mammals, each containing one of the desired transgenic phenotypes. Such animals are bred together through a series of crosses, backcrosses and selections, to ultimately generate a single animal containing all desired knockout constructs and/or expression constructs, where the animal is otherwise congenic (genetically identical) to the wild type except for the presence of the knockout construct(s) and/or transgene(s).

The present invention is further illustrated by the following examples which should not be construed as limiting in any way. The contents of all cited references (including literature references, issued patents, published patent applications as cited throughout this application are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames and S. J. Higgins eds.; *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I–IV (D. M. Weir and C. C. Blackwell, eds., 1986); *Manipulating the Mouse Embryo* (Cold Spring Harbor Laboratory Press, Cold Spring Harbor, N.Y., 1986).

EXAMPLES

Identification of Tub Interactors

The following materials and methods were used in the Examples:

Yeast strains, Media, and Microbiological Techniques

Standard yeast media including synthetic complete medium lacking L-leucine, L-tryptophan, and L-histidine were prepared and yeast genetic manipulations were performed as described (Sherman (1991) *Meth. Enzymol.* 194:3–21). Yeast transformations were performed using standard protocols (Gietz et al. (1992) *Nucl. Acids Res.* 20:1425. Ito et al, (1983) *J. Bacteriol.* 153:163–168). Plasmid DNAs were isolated from yeast strains by a standard method (Hoffman and Winston (1987) *Gene* 57:267–272).

Western Blotting

A total protein extract of TB14 and TB20 was subjected to Western blotting analysis to confirm and qualitatively evaluate expression of the GAL4 DNA-binding domain TUB fusion proteins. The protein extract were prepared by growing TB14 and TB20 in synthetic complete medium lacking L-tryptophan (Sherman (1991) *Meth. Enzymol.* 194:3) to an $OD_{600}$ of 1. The yeast cells from 4.5 ml of culture were collected by centrifugation and the cell pellet was resuspended in 1 ml of 0.25 M NaOH 1% betamercaptoethanol and incubated at 4° C. for 10 minutes. 160 ml of 50% TCA were then added to the cell suspension and after mixing the suspension was incubated at 4° C. for 10 minutes. The suspension was then microfuged at 4° C. for 10 minutes, the supernatant fraction was discarded, and the pellet was washed with cold acetone, air dried, and then resuspended in 120 ml of 2×tris-glycine SDS sample buffer (Novex, San Diego, Calif.) diluted to 1×strength with deionized water.

15 μl of the sample was boiled for 2 minutes and then electrophoresed on a 14% tris glycine SDS polyacrylamide gel (Novex) and then transferred to an immobilon PVDF membrane (Millipore; San Francisco, Calif.). The primary antibody utilized was a rabbit anti-yeast GAL4 DNA-binding domain polyclonal antibody (Upstate Biotechnology Inc., Lake Placid, N.Y.) and the secondary antibody was a donkey anti-rabbit Ig, peroxidase linked species-specific whole antibody (Amersham Life Sciences, Cleveland, Ohio). Western blotting procedures were essentially as described (Sambrook et al. Molecular Cloning 2nd edition. Cold Spring Harbor Laboratory Press. 1989) and proteins interacting with the antibodies were visualized using the ECL detection system (Amersham Life Sciences, Cleveland, Ohio), essentially as described by the manufacturer. Expression of the GAL4 DNA-binding domain TUB cytoplasmic domain fusion proteins were detected.

Beta Galactosidase Assays

The filter disk beta-galactosidase (beta-gal) assay was performed essentially as previously described (Brill et al. (1994) *Mol. Biol. Cell.* 5:297–312). Briefly, strains to be tested were grown as patches of cells on appropriate medium dictated by the experiment at 30° C. overnight. The patches or colonies of cells were replica plated to Whatman #50 paper disks (Schleicher & Schuell, #576; Keene, N.H.) that had been placed on the test medium in petri dishes. After growth overnight at 30° C., the paper disks were removed from the plates and the cells on them were permeabilized by immediately immersing them in liquid nitrogen for 30 seconds. After this treatment, the paper disks were thawed at room temperature for 20 seconds and then placed in petri dishes that contained a disk of Whatman #3 paper (Schleicher & Schuell, #593, Keene, N.H.) saturated with 2.5 ml of Z buffer containing 37 μl of 2% weight per volume of the chromogenic beta-gal substrate X-gal. The permeabilized strains on the paper disks were incubated at 30° C. and inspected at timed intervals for the blue color diagnostic of beta-gal activity in this assay. The assay was stopped by removing the paper disk containing the patches of cells and air drying it.

Two Hybrid Screening and Identification of Tub Interactors

Human TUB 184-506 and human TUB 1-506 were cloned into pGBT9 (Clontech, Palo Alto, Calif.). The human TUB 184-506 was called pGBhTUB and the human TUB 1-506 clone was called pMB71. pGBhTUB and pMB71 were transformed into two-hybrid screening strain HF7c. A pGBhTUB transformant was called TB14 and a pMB71 transformant was called TB20. It was verified that neither human TUB 184-506 nor human TUB 1-506 activated the HIS3 or lacZ reporter genes present in HF7c. Protein extracts from TB14 and TB20 were subjected to Western blot analysis. Human TUB 184-506 was expressed at a high level and human TUB 1-506 was expressed at a very low level.

In one experiment, TB14 was transformed with a human prostate two-hybrid library and 20 million transformants were obtained and in another experiment TB14 was transformed with a mouse T-cell library and 10 million transformants were obtained. TB20 was transformed with a human prostate two-hybrid library and 1.5 million transformants were obtained. By PCR with TUB-specific primers, it was determined that the TUB cDNA was present in these libraries. Transformants were plated on synthetic complete medium lacking leucine, tryptophan, and histidine to select for transformants expressing cDNA library plasmids encoding TUB-interacting proteins. All colonies that grew on the selective plates were analyzed for beta-galactosidase expression using the filter beta-galactosidase assay and the strongest beta-galactosidase expressing plasmids from each screen were analyzed.

In the screen where TB14 was transformed with a human prostate two-hybrid library, E. coli plasmid ptyhq058; E. coli plasmid ptyhq054 and E. coli plasmid ptyhq036 were identified. In the screen where TB14 was transformed with a mouse T-cell library, E. coli plasmid ptyht101 and E. coli plasmid ptyht102, the mouse homologues of E. coli plasmid ptyhq036 and E. coli plasmid ptyhq054 were identified. In the screen where TB20 was transformed with the human prostate library, E. coli plasmid ptyhq049 and human serine palmitoyl transferase (GenBank Accession No. U15555) were identified. Human serine palmitoyl transferase is a weak interactor because it activates the HIS3 reporter gene but not the lacZ gene, at least not enough to be detected in the assays. E. coli plasmid ptyhq058 appeared to be the strongest interactor. All seven of these interactors bind to full length human and mouse TUB and the carboxyl-terminus of human and mouse TUB. In addition, none of these interactors bind to the carboxyl-terminus of human and mouse TUB missing the final 44 amino acids, amino acids lacking in the mutated mouse TUB gene. These seven interactors were found to not bind to several test proteins showing that they bind specifically to TUB.

Northern Analysis

Methods

Total RNA was isolated from various mouse (C57BL/6 wild type and tub/tub) tissues using RNAzol B (Tel-Test, Inc., Friendswood, Tex.). Poly A+ RNA was isolated from a variety of human and mouse cell lines using the FastTrack system (Invitrogen, San Diego, Calif.). Extracted RNA was electrophoresed through a formaldehyde gel, transferred to Genescreen nylon membrane (NEN Research Products, Boston, Mass.) and cross-liked using a Stratalinker apparatus (Stratagene, La Jolla, Calif.).

For probing northern blots, 50 ng of the following probes were labelled using Prime-It (Stratagene, La Jolla, Calif.): human ank; human tpr; human ring; mouse tpr; or mouse ring. Blots were hybridized at 65° C. in Church Buffer overnight and washed in 0.2×SSC/0.1% SDS also at 65° C. Filters were exposed to film (X-omat AR, Kodak) for 18–36 hours.

Human Tissue Results

Human multiple tissue northern blots (Clontech, Palo Alto, Calif.) were probed. The human tissues tested included: spleen, thymus, prostate, testes, uterus, small intestine, colon, peripheral blood leukocytes, heart, brain, placenta, lung, liver, skeletal muscle, kidney, pancreas and retina.

Bands of approximately 2.4 kb and 10 kb were found to be ubiquitously expressed in all tissues tested using the human ank probe. The 2.4 kb band in retinal tissue gave an increased signal. Using the human ring probe, bands of 1.3 kb and 2 kb were expressed in all tissues tested. The 2 kb band gave an increased signal in retinal tissue. Hybridization with the human ring probe yielded bands of 3 kb and 4 kb in all tissues tested. An additional band of 1.4 kb was detected in testes.

Mouse Tissue Results

Mouse tissues were obtained from C57BL/6 and tub/tub animals. Tissues used were: brain, hypothalamus, liver, heart, spleen, stomach, kidney, muscle, fat, and testes. Neither the human ring probe nor the human ank probe yielded any signal in any tissue tested. the mouse tpr probe hybridized with a 1.4 kb band in C57BL/6 testes and a 1.4 kb band in tub/tub brain and testes. The mouse ring probe hybridized with a 2.4 kb and a 3.0 kb band in all tissues tested from both strains of mice and also hybridized with a 1.4 kb band from testes tissue from C57BL/6 and tub/tub mice.

Cell Line Results

Poly A+ RNA was isolated from a variety of ATCC cell lines (including human cell lines SHEP; SHSY5Y; SKNMC (neuroblastoma); SKNSH; Neuro 2A (neuroblastoma), NB412A/8; the human breast carcinoma cell line MCF7 and the mouse fibroblast cell line NIH 3T3). The human ank probe hybridized with a 2.3 kb band in the SHEP, SHSY5Y, SKNMC, SKNSH, and MCF7 cell lines. The same human ank probe lit up a 2 kb band in Neuro 2A and NB412A/8 cells. No signal was detected in the 3T3 cell line. The human tpr probe hybridized with a 2 kb band in all cell lines tested. An additional band of 4.4 kb was detected using this probe in the neuro 2A cells. The human ring probe detected a 2.4 kb band in the SHEP, SHSY5Y, SKNMC, and SKNSH cell lines. No signal was detected in any other of the cell lines using the ring probe.

Deposit of Microorganisms

E. coli plasmid ptyhq049 was deposited with the American Type Culture Collection 10801 University Boulevard, Manassas, Va. 20110-2209, on Aug. 6 1996 under the terms of the Budapest Treaty and assigned Accession Number 98125 (hTI-1) (SEQ ID NO:1).

E. coli plasmid ptyhq058 was deposited with the American Type Culture Collection 10801 University Boulevard, Manassas, Va. 20110-2209, on Aug. 6 1996 under the terms of the Budapest Treaty and assigned Accession Number 98127 (hTI-2) (SEQ ID NO:2).

E. coli plasmid ptyhq036 was deposited with the American Type Culture Collection 10801 University Boulevard, Manassas, Va. 20110-2209, on Aug. 6 1996 under the terms of the Budapest Treaty and assigned Accession Number 98128 (hTI-3) (SEQ ID NO:3).

E. coli plasmid ptyhq054 was deposited with the American Type Culture Collection 10801 University Boulevard, Manassas, Va. 20110-2209, on Aug. 6 1996 under the terms of the Budapest Treaty and assigned Accession Number 98126 (hTI-4) (SEQ ID NO:5).

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. An isolated polypeptide comprising the amino acid sequence of SEQ ID NO:31.

2. An isolated polypeptide comprising the amino acid sequence of SEQ ID NO:32.

3. An isolated polypeptide comprising the amino acid sequence of SEQ ID NO:33.

4. An isolated polypeptide comprising the amino acid sequence of SEQ ID NO:34.

5. An isolated polypeptide comprising the amino acid sequence of SEQ ID NO:35.

6. An isolated polypeptide comprising the amino acid sequence of SEQ ID NO:36.

7. An isolated polypeptide consisting of the amino acid sequence of SEQ ID NO:31.

8. An isolated polypeptide consisting of the amino acid sequence of SEQ ID NO:32.

9. An isolated polypeptide consisting of the amino acid sequence of SEQ ID NO:33.

10. An isolated polypeptide consisting of the amino acid sequence of SEQ ID NO:34.

11. An isolated polypeptide consisting of the amino acid sequence of SEQ ID NO:35.

12. An isolated polypeptide consisting of the amino acid sequence of SEQ ID NO:36.

13. An isolated polypeptide comprising an amino acid sequence encoded by the nucleotide sequence of the DNA insert of the plasmid deposited with ATCC as Accession Number 98125.

14. An isolated polypeptide comprising an amino acid sequence encoded by the nucleotide sequence of the DNA insert of the plasmid deposited with ATCC as Accession Number 98126.

15. An isolated polypeptide comprising an amino acid sequence encoded by the nucleotide sequence of the DNA insert of the plasmid deposited with ATCC as Accession Number 98127.

16. An isolated polypeptide comprising an amino acid sequence encoded by the nucleotide sequence of the DNA insert of the plasmid deposited with ATCC as Accession Number 98128.

17. An isolated naturally occurring allelic variant of a polypeptide comprising the amino acid sequence of SEQ ID NO:31, wherein the naturally occurring allelic variant is encoded by a nucleic acid molecule which hybridizes to a complement of a nucleic acid molecule consisting of SEQ ID NO:1, in 6×SSC at 45° C., followed by one or more washes in 0.2×SSC, 0.1% SDS at 65° C.

18. An isolated naturally occurring allelic variant of a polypeptide comprising the amino acid sequence of SEQ ID NO:32, wherein the naturally occurring allelic variant is encoded by a nucleic acid molecule which hybridizes to a complement of a nucleic acid molecule consisting of SEQ ID NO:2, in 6×SSC at 45° C., followed by one or more washes in 0.2×SSC, 0.1% SDS at 65° C.

19. An isolated naturally occurring allelic variant of a polypeptide comprising the amino acid sequence of SEQ ID NO:33, wherein the naturally occurring allelic variant is encoded by a nucleic acid molecule which hybridizes to a complement of a nucleic acid molecule consisting of SEQ ID NO:3, in 6×SSC at 45° C., followed by one or more washes in 0.2×SSC, 0.1% SDS at 65° C.

20. An isolated naturally occurring allelic variant of a polypeptide comprising the amino acid sequence of SEQ ID NO:34, wherein the naturally occurring allelic variant is encoded by a nucleic acid molecule which hybridizes to a complement of a nucleic acid molecule consisting of SEQ ID NO:4, in 6×SSC at 45° C., followed by one or more washes in 0.2×SSC, 0.1% SDS at 65° C.

21. An isolated naturally occurring allelic variant of a polypeptide comprising the amino acid sequence of SEQ ID NO:35, wherein the naturally occurring allelic variant is encoded by a nucleic acid molecule which hybridizes to a complement of a nucleic acid molecule consisting of SEQ ID NO:5, in 6×SSC at 45° C., followed by one or more washes in 0.2×SSC, 0.1% SDS at 65° C.

22. An isolated naturally occurring allelic variant of a polypeptide comprising the amino acid sequence of SEQ ID NO:36, wherein the naturally occurring allelic variant is encoded by a nucleic acid molecule which hybridizes to a complement of a nucleic acid molecule consisting of SEQ ID NO:6, in 6×SSC at 45° C., followed by one or more washes in 0.2×SSC, 0.1% SDS at 65° C.

23. An isolated naturally occurring allelic variant of a polypeptide consisting of the amino acid sequence of SEQ ID NO:31, wherein the naturally occurring allelic variant is encoded by a nucleic acid molecule which hybridizes to a complement of a nucleic acid molecule consisting of SEQ ID NO:1, in 6×SSC at 45° C., followed by one or more washes in 0.2×SSC, 0.1% SDS at 65° C.

24. An isolated naturally occurring allelic variant of a polypeptide consisting of the amino acid sequence of SEQ ID NO:32, wherein the naturally occurring allelic variant is encoded by a nucleic acid molecule which hybridizes to a complement of a nucleic acid molecule consisting of SEQ ID NO:2, in 6×SSC at 45° C., followed by one or more washes in 0.2×SSC, 0.1% SDS at 65° C.

25. An isolated naturally occurring allelic variant of a polypeptide consisting of the amino acid sequence of SEQ ID NO:33, wherein the naturally occurring allelic variant is encoded by a nucleic acid molecule which hybridizes to a complement of a nucleic acid molecule consisting of SEQ ID NO:3, in 6×SSC at 45° C., followed by one or more washes in 0.2×SSC, 0.1% SDS at 65° C.

26. An isolated naturally occurring allelic variant of a polypeptide consisting of the amino acid sequence of SEQ ID NO:34, wherein the naturally occurring allelic variant is encoded by a nucleic acid molecule which hybridizes to a complement of a nucleic acid molecule consisting of SEQ ID NO:4, in 6×SSC at 45° C., followed by one or more washes in 0.2×SSC, 0.1% SDS at 65° C.

27. An isolated naturally occurring allelic variant of a polypeptide consisting of the amino acid sequence of SEQ ID NO:35, wherein the naturally occurring allelic variant is encoded by a nucleic acid molecule which hybridizes to a complement of a nucleic acid molecule consisting of SEQ ID NO:5, in 6×SSC at 45° C., followed by one or more washes in 0.2×SSC, 0.1% SDS at 65° C.

28. An isolated naturally occurring allelic variant of a polypeptide consisting of the amino acid sequence of SEQ ID NO:36, wherein the naturally occurring allelic variant is encoded by a nucleic acid molecule which hybridizes to a complement of a nucleic acid molecule consisting of SEQ ID NO:6, in 6×SSC at 45° C., followed by one or more washes in 0.2×SSC, 0.1% SDS at 65° C.

29. An isolated fusion polypeptide comprising the polypeptide of any one of claims 1–27 or 28, operatively linked to a heterologous polypeptide.

30. An isolated naturally occurring allelic variant of a polypeptide comprising the amino acid sequence of SEQ ID NO:31, wherein the naturally occurring allelic variant is encoded by a nucleic acid molecule which hybridizes to a complement of a nucleic acid molecule consisting of SEQ ID NO:1, in 6×SSC at 45° C., followed by one or more washes in 0.2×SSC, 0.1% SDS at 65° C., wherein the naturally occurring allelic variant binds a Tub interactor protein.

31. An isolated naturally occurring allelic variant of a polypeptide comprising the amino acid sequence of SEQ ID NO:32, wherein the naturally occurring allelic variant is encoded by a nucleic acid molecule which hybridizes to a complement of a nucleic acid molecule consisting of SEQ ID NO:2, in 6×SSC at 45° C., followed by one or more washes in 0.2×SSC, 0.1% SDS at 65° C., wherein the naturally occurring allelic variant binds a Tub interactor protein.

32. An isolated naturally occurring allelic variant of a polypeptide comprising the amino acid sequence of SEQ ID NO:33, wherein the naturally occurring allelic variant is encoded by a nucleic acid molecule which hybridizes to a complement of a nucleic acid molecule consisting of SEQ ID NO:3, in 6×SSC at 45° C., followed by one or more washes in 0.2×SSC, 0.1% SDS at 65° C., wherein the naturally occurring allelic variant binds a Tub interactor protein.

33. An isolated naturally occurring allelic variant of a polypeptide comprising the amino acid sequence of SEQ ID NO:34, wherein the naturally occurring allelic variant is encoded by a nucleic acid molecule which hybridizes to a complement of a nucleic acid molecule consisting of SEQ ID NO:4, in 6×SSC at 45° C., followed by one or more washes in 0.2×SSC, 0.1% SDS at 65° C., wherein the naturally occurring allelic variant binds a Tub interactor protein.

34. An isolated naturally occurring allelic variant of a polypeptide comprising the amino acid sequence of SEQ ID NO:35, wherein the naturally occurring allelic variant is encoded by a nucleic acid molecule which hybridizes to a complement of a nucleic acid molecule consisting of SEQ ID NO:5, in 6×SSC at 45° C., followed by one or more washes in 0.2×SSC, 0.1% SDS at 65° C., wherein the naturally occurring allelic variant binds a Tub interactor protein.

35. An isolated naturally occurring allelic variant of a polypeptide comprising the amino acid sequence of SEQ ID NO:36, wherein the naturally occurring allelic variant is encoded by a nucleic acid molecule which hybridizes to a complement of a nucleic acid molecule consisting of SEQ ID NO:6, in 6×SSC at 45° C., followed by one or more washes in 0.2×SSC, 0.1% SDS at 65° C., wherein the naturally occurring allelic variant binds a Tub interactor protein.

36. An isolated Tub interactor binding polypeptide encoded by a nucleic acid molecule which hybridizes to a complement of a nucleic acid molecule consisting of SEQ ID NO:1, in 6×SSC at 45° C., followed by one or more washes in 0.2×SSC, 0.1% SDS at 50–65° C.

37. An isolated Tub interactor binding polypeptide encoded by a nucleic acid molecule which hybridizes to a complement of a nucleic acid molecule consisting of SEQ ID NO:2, in 6×SSC at 45° C., followed by one or more washes in 0.2×SSC, 0.1% SDS at 50–65° C.

38. An isolated Tub interactor binding polypeptide encoded by a nucleic acid molecule which hybridizes to a complement of a nucleic acid molecule consisting of SEQ ID NO:3, in 6×SSC at 45° C., followed by one or more washes in 0.2×SSC, 0.1% SDS at 50–65° C.

39. An isolated Tub interactor binding polypeptide encoded by a nucleic acid molecule which hybridizes to a complement of a nucleic acid molecule consisting of SEQ ID NO:4, in 6×SSC at 45° C., followed by one or more washes in 0.2×SSC, 0.1% SDS at 50–65° C.

40. An isolated Tub interactor binding polypeptide encoded by a nucleic acid molecule which hybridizes to a complement of a nucleic acid molecule consisting of SEQ ID NO:5, in 6×SSC at 45° C., followed by one or more washes in 0.2×SSC, 0.1% SDS at 50–65° C.

41. An isolated Tub interactor binding polypeptide encoded by a nucleic acid molecule which hybridizes to a complement of a nucleic acid molecule consisting of SEQ ID NO:6, in 6×SSC at 45° C., followed by one or more washes in 0.2×SSC, 0.1% SDS at 50–65° C.

* * * * *